US008247594B2

(12) United States Patent
Jung et al.

(10) Patent No.: US 8,247,594 B2
(45) Date of Patent: Aug. 21, 2012

(54) INSECTICIDAL COMPOUNDS

(75) Inventors: Pierre Joseph Marcel Jung, Stein (CH); Christopher Richard Ayles Godfrey, Stein (CH); William Lutz, Stein (CH); Peter Maienfisch, Stein (CH); André Denis Stoller, Stein (CH); Werner Zambach, Stein (CH)

(73) Assignee: Syngenta Crop Protection LLC, Greensboro, NC (US)

( * ) Notice: Subject to any disclaimer, the term of this patent is extended or adjusted under 35 U.S.C. 154(b) by 0 days.

(21) Appl. No.: 12/530,007

(22) PCT Filed: Feb. 26, 2008

(86) PCT No.: PCT/EP2008/001489
§ 371 (c)(1),
(2), (4) Date: Jan. 26, 2010

(87) PCT Pub. No.: WO2008/107091
PCT Pub. Date: Sep. 12, 2008

(65) Prior Publication Data
US 2010/0130601 A1 May 27, 2010

(30) Foreign Application Priority Data

Mar. 7, 2007 (GB) .................................... 0704468.8

(51) Int. Cl.
C07C 261/00 (2006.01)
C07C 269/00 (2006.01)
C07C 271/00 (2006.01)
A01N 43/60 (2006.01)
A01N 43/40 (2006.01)
A01N 47/46 (2006.01)
A01N 47/48 (2006.01)

(52) U.S. Cl. ........... 560/29; 504/235; 504/244; 504/308

(58) Field of Classification Search .................... None
See application file for complete search history.

(56) References Cited

U.S. PATENT DOCUMENTS

2007/0027154 A1* 2/2007 Yoshida et al. ............... 514/241

FOREIGN PATENT DOCUMENTS

| EP | 1661886 | 5/2006 |
| JP | 2006225340 | 8/2006 |
| WO | 2004067528 | 8/2004 |

OTHER PUBLICATIONS

Silverman (The Organic Chemistry of Drug Design and Drug Action, 1992, Academic Press Inc.).*
Clark, James et al; Aromatic Thiocyanation using Supported Copper (1) Thiocyanate; Journal of the Chemical Society, Chemical Communications, (2), 81-2; 1989.
Reeves, W. Preston et al; Phase Transfer Catalysis Preparation of Aryl Thiocyanates; Synthetic Communications, 10 (8), 633-6; 1980.
Bentley, Dagmar et al; Chemical Development of ZD9331: Synthesis of a Bromomethylquinazolinone Avoiding a Nonselective Radical Bromination; Organic Process Research and Development (2006), 10(3), 553-555.
Lee, Jae Hak et al; Acetonitride-Mediated Synthesis of 2,4-Dichloroquinoline from 2-Ethynylaniline and 2,4-Dichloroquinazoline from Anthranilonitrile; Synlett (2006), (1), 65-68.
Tschaen, D.M. et al; An Improved Procedure for Aromatic Cyanation; Journal of Medicinal Chemistry (2004), 47(8), 1969.
Jiang, Biao et al; Synthesis of Dialkyl Cyanoboronates and their Application in Palladium-Catalyzed Cyanation of Aryl Halides; Tetrahedron (2001, 57(8), 1581.
Jian, Fang Fang et al; Synthesis, Structure and Quantum Chemical Calculations on p-trifluoromethylphenyl thioacid amide; Journal of Fluorine Chemistry (2006), 127(1), 63-67.
Kaboudin, Babak et al; Phosphorus Pentasulfide: A Mild and Versatile Reagent for the Preparation of Thiomides from Nitriles; Synthesis (2006), (2), 224-226.
Moghaddam, Firouz Matloubi et al; Microware-Assisted Conversion of Nitriles to Thiomides in Solvent-Free Condition; Synthetic Communications (2003), 33(24), 4279-4284.
Manaka, Akira et al; Synthesis of Aromatic Thiomide from Nitrile Without Handling of Gaseous Hydrogen Sulfide; Synthetic Communications (2005), 35(5), 761-764.
Katritzky, Alan R. et al; A General Method for the N-Alkylation of Thiomides; Tetrahedron Letters (1988), 29(15), 1755-8.
Bassindale, Alan R. et al; Chemoselective Methylation of Amides and Heterocycles Using Chloromethyldimethylsilyl Chloride; Tetrahedron Letters (2000), 41(25), 4933.
Sellstedt, John H. et al; Oxanilic Acids, a New Series of Orally Active Antiallergic Agents; Journal of Medicinal Chemistry (1975), 18(9), 926.

(Continued)

Primary Examiner — Susanna Moore
Assistant Examiner — Jennifer C Sawyer
(74) Attorney, Agent, or Firm — William A. Teoli, Jr.

(57) ABSTRACT

A compound of formula (I), wherein $A^1$, $A^2$, $A^3$, $A^4$, $R^1$, $R^2$, $R^3$, $G^1$, $G^2$, $G^3$ and Q are as defined in claim 1; or a salt or N-oxide thereof. Furthermore, the present invention relates to processes and intermediates for preparing compounds of formula (I), to insecticidal, acaricidal, molluscicidal and nematicidal compositions comprising them and to methods of using them to combat and control insect, acarine, mollusc and nematode pests.

(I)

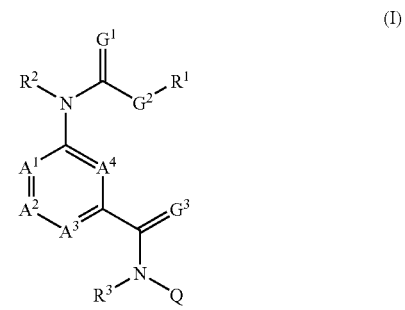

20 Claims, No Drawings

OTHER PUBLICATIONS

Braddock, D. Christopher et al; Ortho-Substituted Iodobenzenes as Novel Organocatalysts for Bromination of Alkenes; Chemical Communications (Cambridge, United Kingdom) (2006), (23), 2483.

Wang, Xiang et al; Platinum Catalyzed Intermolecular Hydroamination of Unactivated Olefins with Carboxamides; Organimetallics (2004), 23(8), 1649-1651.

Fache, Fabienne et al; Extension of the Eschweiler-Clarke Procedure to the N-Alkylation of Amides; Tetrahedron Letters (1994), 35(20), 3313-14.

Sukata, Kazuaki; The Selective N-Monoalkylation of Amides with Alkyl Halides in the Presence of Alumina and KOH; Bulletin of the Chemical Society of Japan (1985), 58(3), 838-843.

Wissner, Allan et al; 2-(Quinazolin-4-ylamino)-[1,4] benzoquinones as Covalent-Binding, Irreversible Inhibitors of the Kinase Domain of Vascular Endothelial Growth Factor Receptor-2; Journal of Medicinal Chemistry (2005), 48(24), 7560.

Quan, Mimi L. et al; Discovery of 1-(3'-Aminobenzisoxazol-5'yl)-3-trifluormethyl-N-[2-fluoro-4-[(2' dimethylaminomethyl) imidazol-1-yl]phenyl]-1H-pyrazole-5-carboxyamide Hydrochloride (Razaxaban), a Highly Potent, Selective and Orally Bioavailable Factor Xa Inhibitor; Journal of Medicinal Chemistry (2005), 48(6), 1729.

Jung, Frederic H. et al; Discovery of Novel and Potent Thiazoloquinazolines as Selective Aurora A and B Kinase Inhibitors; Journal of Medicinal Chemistry (2006), 49(3), 955-970.

Wu, Chengde et al; Discovery, Modeling, and Human Pharmacokinetics of N-(2-Acetyl-4,6-dimethylphenyl)-3-(3,4-dimethylisoxazol-5-ylsulfamoyl)-thiophene-2-carboxamide (TBC3711), a Second Generation, ETA Selective, and Orally Bioavailable Endothelin Antagonist1; Journal of Medicinal Chemistry (2004), 47(8), 1969.

Silverman, Richard B., "Organic Chemistry of Drug Design and Drug Action", Eliesever Academic Press, Chapter 2, pp. 28-33, 2004.

Stringer, A, et al. "Insecticidal Activity and Chemical Constitution: Analogues and Isosteres of DDT", Ann. Appl. Biol., vol. 43 (3), pp. 366-378, 1955.

\* cited by examiner

INSECTICIDAL COMPOUNDS

This application is a 371 of International Application No. PCT/EP2008/001489 filed Feb. 26, 2008, which claims priority to GB 0704468.8 filed Mar. 7, 2007, the contents of which are incorporated herein by reference.

The present invention relates to certain carboxamide derivatives, to processes and intermediates for preparing them, to insecticidal, acaricidal, molluscicidal and nematicidal compositions comprising them and to methods of using them to combat and control insect, acarine, mollusc and nematode pests.

Aromatic amide derivatives with insecticidal properties are disclosed, for example, in WO 05/021488 and JP 2006/225340.

It has now surprisingly been found that certain carboxamide derivatives which have at least one cyano, thiocyanato, aminothiocarbonyl, N—$C_1$-$C_4$alkyl-aminothiocarbonyl or N,N-di-$C_1$-$C_4$alkyl-aminothiocarbonyl substituent in the central aromatic ring have insecticidal properties.

The present invention therefore provides a compound of formula (I):

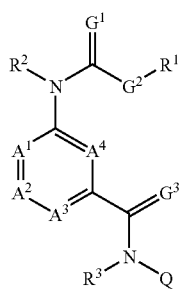

(I)

wherein $A^1$, $A^2$, $A^3$ and $A^4$ are independently of each other C—$R^4$, C—$R^5$ or nitrogen, provided that at least one of $A^1$, $A^2$, $A^3$ and $A^4$ is C—$R^4$ and no more than two of $A^1$, $A^2$, $A^3$ and $A^4$ are nitrogen;

$R^1$ is $C_1$-$C_6$alkyl, $C_1$-$C_6$haloalkyl, $C_2$-$C_6$alkenyl, $C_2$-$C_6$haloalkenyl, $C_2$-$C_6$alkynyl, $C_2$-$C_6$haloalkynyl, $C_3$-$C_8$cycloalkyl, $C_3$-$C_8$halocycloalkyl, or -$E^1$-$Z^1$—$R^6$ wherein $E^1$ its $C_1$-$C_4$alkylene, $C_2$-$C_4$alkenylene, $C_3$-$C_4$alkynylene, $C_1$-$C_4$haloalkylene, $C_2$-$C_4$haloalkenylene, or $C_3$-$C_4$haloalkynylene, $Z^1$ is —O—, —S—, —SO—, or —$SO_2$—, and $R^6$ is hydrogen, $C_1$-$C_6$alkyl, $C_2$-$C_6$alkenyl, $C_2$-$C_6$alkynyl, $C_1$-$C_6$haloalkyl, $C_2$-$C_6$haloalkenyl, $C_2$-$C_6$haloalkynyl, or -$E^2$-$R^7$ wherein $E^2$ is $C_1$-$C_4$alkylene, $C_2$-$C_4$alkenylene, $C_3$-$C_4$alkynylene, $C_1$-$C_4$haloalkylene, $C_2$-$C_4$haloalkenylene, or $C_3$-$C_4$haloalkynylene, and $R^7$ is $C_3$-$C_8$cycloalkyl, $C_3$-$C_8$halocycloalkyl, cyano, nitro, hydroxyl, or phenyl or phenyl substituted by one to five substituents $R^8$, which may be the same or different, or pyridyl or pyridyl substituted with one to four substituents $R^9$, which may be the same or different, or thiophenyl, or tetrahydrofuranyl;

$R^2$ and $R^3$ are independently of each other hydrogen, $C_1$-$C_4$alkyl, $C_2$-$C_4$alkenyl, $C_2$-$C_4$alkynyl, $C_1$-$C_4$alkylcarbonyl, $C_1$-$C_4$haloalkylcarbonyl, hydroxy, $C_1$-$C_4$alkylcarbonyloxy, arylcarbonyl-oxy or arylcarbonyloxy wherein the aryl ring is substituted by one to five substituents independently selected from halogen, $C_1$-$C_4$alkyl, $C_1$-$C_4$haloalkyl, $C_1$-$C_4$alkoxy or $C_1$-$C_4$haloalkoxy;

$G^1$, $G^2$ and $G^3$ are independently of each other oxygen or sulfur;

each $R^4$ is independently cyano, thiocyanato, aminothiocarbonyl, N—$C_1$-$C_4$alkyl-amino-thiocarbonyl or N,N-di-$C_1$-$C_4$alkyl-aminothiocarbonyl;

each $R^5$ is independently hydrogen, halogen, $C_1$-$C_4$alkyl, $C_1$-$C_4$haloalkyl or $C_1$-$C_4$alkoxy;

each $R^8$ is independently halogen, $C_1$-$C_6$alkyl, $C_1$-$C_6$haloalkyl, $C_1$-$C_6$alkoxy, $C_1$-$C_6$halo-alkoxy, $C_1$-$C_6$alkylthio, $C_1$-$C_6$haloalkylthio, $C_1$-$C_6$alkylsulfinyl, $C_1$-$C_6$haloalkylsulfinyl, $C_1$-$C_6$alkylsulfonyl, $C_1$-$C_6$haloalkylsulfonyl, cyano, nitro, hydroxyl, $C_1$-$C_4$alkylcarbonyl, $C_1$-$C_4$haloalkylcarbonyl, $C_1$-$C_4$alkylcarbonyloxy, $C_1$-$C_4$alkoxycarbonyl, or pentafluorosulfanyl;

each $R^9$ is independently halogen, $C_1$-$C_6$alkyl, $C_1$-$C_6$haloalkyl, $C_1$-$C_6$alkoxy, $C_1$-$C_6$halo-alkoxy, $C_1$-$C_6$alkylthio, $C_1$-$C_6$haloalkylthio, $C_1$-$C_6$alkylsulfinyl, $C_1$-$C_6$haloalkylsulfinyl, $C_1$-$C_6$alkylsulfonyl, $C_1$-$C_6$haloalkylsulfonyl, cyano, nitro, hydroxyl, $C_1$-$C_4$alkylcarbonyl, $C_1$-$C_4$haloalkylcarbonyl, $C_1$-$C_4$alkylcarbonyloxy, $C_1$-$C_4$alkoxycarbonyl, or pentafluorosulfanyl; and Q is a moiety of formula (II) or (III)

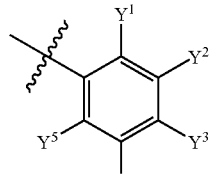

(II)

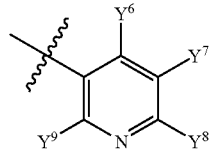

(III)

wherein $Y^1$, $Y^2$, $Y^4$ and $Y^5$ are independently of each other hydrogen, halogen, $C_1$-$C_6$alkyl, $C_1$-$C_6$-haloalkyl, $C_1$-$C_4$ alkoxy-$C_1$-$C_4$-alkyl, $C_1$-$C_6$alkoxy, $C_1$-$C_6$haloalkoxy, $C_1$-$C_6$ alkylthio, $C_1$-$C_6$haloalkylthio, $C_1$-$C_6$alkylsulfinyl, $C_1$-$C_6$haloalkylsulfinyl, $C_1$-$C_6$alkylsulfonyl, $C_1$-$C_6$haloalkylsulfonyl, pentafluorosulfanyl, cyano, or nitro, provided that no more than one of $Y^1$ and $Y^5$ is hydrogen, and $Y^3$ is $C_1$-$C_6$haloalkyl, $C_1$-$C_6$haloalkoxy, $C_1$-$C_6$hydroxyhaloalkyl, $C_1$-$C_6$haloalkylthio, $C_1$-$C_6$haloalkylsulfinyl, $C_1$-$C_6$haloalkylsulfonyl, or pentafluorosulfanyl, or $Y^6$, $Y^7$ and $Y^9$ are independently of each other hydrogen, $C_1$-$C_6$alkyl, $C_1$-$C_6$haloalkyl, $C_1$-$C_4$alkoxy-$C_1$-$C_4$-alkyl, $C_1$-$C_6$alkoxy, $C_1$-$C_6$haloalkoxy, $C_1$-$C_6$alkylthio, $C_1$-$C_6$haloalkylthio, $C_1$-$C_6$alkylsulfinyl, $C_1$-$C_6$haloalkylsulfinyl, $C_1$-$C_6$alkylsulfonyl, $C_1$-$C_6$haloalkylsulfonyl, pentafluorosulfanyl, cyano, or nitro, provided that no more than one of $Y^6$ and $Y^9$ is hydrogen, and $Y^8$ is $C_1$-$C_6$haloalkyl, $C_1$-$C_6$haloalkoxy, $C_1$-$C_6$hydroxyhaloalkyl, $C_1$-$C_6$haloalkylthio, $C_1$-$C_6$haloalkylsulfinyl, $C_1$-$C_6$haloalkylsulfonyl, or pentafluorosulfanyl;

or a salt or N-oxide thereof.

The compounds of formula (I) may exist in different geometric or optical isomers or tautomeric forms. This invention covers all such isomers and tautomers and mixtures thereof in all proportions as well as isotopic forms such as deuterated compounds.

Each alkyl moiety either alone or as part of a larger group (such as alkoxy, alkoxy-carbonyl, alkylcarbonyl or alkylene) is a straight or branched chain and is, for example, methyl, ethyl, n-propyl, n-butyl, iso-propyl, n-butyl, sec-butyl, iso-butyl or tert-butyl. The alkyl groups are preferably $C_1$ to $C_6$ alkyl groups, more preferably $C_1$-$C_4$ and most preferably $C_1$-$C_3$ alkyl groups. Examples of alkylene groups are methylene, ethylene, n- and iso-propylene and n-, sec-, iso- and tert-butylene.

Alkenyl and alkynyl moieties (either alone or as part of a larger group, such as alkenyloxy, alkynyloxy, alkenylene or alkynylene) can be in the form of straight or branched chains, and the alkenyl moieties, where appropriate, can be of either the (E)- or (Z)-configuration. Examples are vinyl, allyl and propargyl. The alkenyl and alkynyl groups are preferably $C_2$ to $C_6$ alkenyl or alkynyl groups, more preferably $C_2$-$C_4$ and most preferably $C_2$-$C_3$ alkenyl or alkynyl groups.

Halogen is fluorine, chlorine, bromine or iodine.

Haloalkyl groups (either alone or as part of a larger group, such as haloalkoxy or haloalkylthio) are alkyl groups which are substituted with one or more of the same or different halogen atoms and are, for example, —$CF_3$, —$CF_2Cl$, —$CH_2CF_3$ or —$CH_2CHF_2$. Perfluoroalkyl groups (either alone or as part of a larger group, such as perfluoroalkylthio) are a particular type of haloalkyl group; they are alkyl groups which are completely substituted with fluorine atoms and are, for example, —$CF_3$, —$CF_2CF_3$ or —$CF(CF_3)_2$.

Hydroxyhaloalkyl groups (either alone or as part of a larger group, such as hydroxyhaloalkoxy or hydroxyhaloalkylthio) are haloalkyl groups which are substituted with one or more hydroxyl groups, for example 1,1,1,3,3,3-hexafluoro-2-hydroxy-prop-2-yl.

Haloalkenyl and haloalkynyl groups (either alone or as part of a larger group, such as haloalkenyloxy or haloalkynyloxy) are alkenyl and alkynyl groups, respectively, which are substituted with one or more of the same or different halogen atoms and are, for example, —CH=$CF_2$, —CCl=CClF or —CClC=H.

Cycloalkyl groups can be in mono- or bi-cyclic form and may optionally be substituted by one or more methyl groups. The cycloalkyl groups preferably contain 3 to 8 carbon atoms, more preferably 3 to 6 carbon atoms. Examples of monocyclic cycloalkyl groups are cyclopropyl, 1-methylcyclopropyl, 2-methylcyclopropyl, cyclobutyl, cyclopentyl and cyclohexyl.

Halocycloalkyl groups are cycloalkyl groups which are substituted with one or more of the same of different halogen atoms and may optionally be substituted by one or more methyl groups. Examples of monocyclic halocycloalkyl groups are 2,2-dichloro-cyclopropyl, 2,2-dichloro-1-methylcyclopropyl and 2-chloro-4-fluorocyclohexyl.

In the context of the present specification the term "aryl" refers to a ring system which may be mono-, bi- or tricyclic. Examples of such rings include phenyl, naphthalenyl, anthracenyl, indenyl or phenanthrenyl. A preferred aryl group is phenyl.

Preferred values of $A^1$, $A^2$, $A^3$, $A^4$, $R^1$, $R^2$, $R^3$, $G^1$, $G^2$, $G^3$, $R^4$, $R^5$, Q, $Y^1$, $Y^2$, $Y^3$, $Y^4$, $Y^5$, $Y^6$, $Y^7$, $Y^8$ and $Y^9$ are, in any combination, as set out below.

Preferably $A^1$ is C—$R^4$ or C—$R^5$.
Preferably $A^2$ is C—$R^4$ or C—$R^5$.
Preferably $A^3$ is C—$R^4$ or C—$R^5$.
Preferably $A^4$ is C—$R^4$ or C—$R^5$.
Preferably one, two or three of $A^1$, $A^2$, $A^3$ and $A^4$ are C—$R^4$, more preferably one or two of $A^1$, $A^2$, $A^3$ and $A^4$ are C—$R^4$, most preferably one of $A^1$, $A^2$, $A^3$ and $A^4$ is C—$R^4$.

Preferably $R^1$ is $C_1$-$C_6$alkyl, $C_1$-$C_6$haloalkyl, $C_2$-$C_6$alkenyl, $C_2$-$C_6$haloalkenyl, $C_2$-$C_6$alkynyl, $C_2$-$C_6$haloalkynyl, $C_3$-$C_8$cycloalkyl, $C_3$-$C_8$halocycloalkyl, or cyano-$C_1$-$C_4$alkylene, more preferably $C_1$-$C_6$alkyl, $C_1$-$C_6$haloalkyl, $C_2$-$C_6$alkenyl or cyano-$C_1$-$C_4$alkylene, most preferably methyl, ethyl, 2-fluoro-ethyl, 2-chloro-ethyl, 2-bromo-ethyl, 2-iodo-ethyl, 2-cyano-ethyl, 2,2-difluoro-ethyl, 2,2-dichloro-ethyl, 2,2,2-trifluoro-ethyl, 2,2,2-trichloro-ethyl, 2,2,2-tribromo-ethyl, propyl, 3-fluoro-propyl, 3-chloro-propyl, 3-bromo-propyl, 1,2-difluoro-prop-2-yl, 1,3-difluoro-prop-2-yl, 1,3-dichloro-prop-2-yl, 1-chloro-3-fluoro-prop-2-yl, 3,3,3-trifluoro-propyl, butyl, 4,4,4-trifluoro-butyl or vinyl.

Preferably $R^2$ is hydrogen, methyl, ethyl, allyl, propargyl, acetyl, 3,3,3-trichloro-propionyl, hydroxy, acetyloxy or benzoyloxy.

More preferably $R^2$ is hydrogen, methyl, ethyl, allyl, propargyl, acetyl or hydroxy.

Even preferably $R^2$ is hydrogen, methyl or ethyl.

Yet even more preferably $R^2$ is hydrogen or methyl.

Most preferably $R^2$ is hydrogen.

Preferably $R^3$ is hydrogen, methyl, ethyl, allyl, propargyl, acetyl, hydroxy, acetyloxy or benzoyloxy.

More preferably $R^3$ is hydrogen, methyl, ethyl, allyl, propargyl, acetyl or hydroxy.

Even preferably $R^3$ is hydrogen, methyl or ethyl.

Yet even more preferably $R^3$ is hydrogen or methyl.

Most preferably $R^3$ is hydrogen.

Preferably $G^1$ is oxygen.
Preferably $G^2$ is oxygen.
Preferably $G^3$ is oxygen.

Preferably each $R^4$ is independently cyano, thiocyanato or aminothiocarbonyl, more preferably cyano or thiocyanato, most preferably cyano.

Preferably each $R^5$ is independently hydrogen, fluoro, chloro, bromo, methyl, trifluoromethyl or methoxy.

More preferably each $R^5$ is independently hydrogen, fluoro, chloro, bromo, methyl or trifluoromethyl.

Even more preferably each $R^5$ is independently hydrogen, fluoro, methyl or trifluoromethyl.

Yet even more preferably each $R^5$ is independently hydrogen or fluoro.

Most preferably each $R^5$ is hydrogen.

Preferably Q is a moiety of formula (II).

Preferably $Y^1$ is cyano, halogen, methyl, ethyl, trifluoromethyl or methoxymethyl.

More preferably $Y^1$ is cyano, bromo, chloro, methyl, ethyl, trifluoromethyl or methoxymethyl.

Even more preferably $Y^1$ is bromo, chloro, methyl, ethyl or methoxymethyl.

Yet even more preferably $Y^1$ is bromo, methyl or ethyl.

Even more preferably $Y^1$ is methyl or ethyl.

Most preferably $Y^1$ is methyl.

Preferably $Y^2$ is hydrogen, chloro, fluoro or methyl.

Most preferably $Y^2$ is hydrogen.

Preferably $Y^3$ is heptafluoropropyl, heptafluoroprop-2-yl, heptafluoropropylthio, heptafluoropropylsulfinyl, heptafluoropropylsulfonyl, heptafluoroprop-2-ylthio, heptafluoroprop-2-ylsulfinyl, heptafluoroprop-2-ylsulfonyl or nonafluorobut-2-yl.

In one embodiment $Y^3$ is $C_2$-$C_6$perfluoroalkyl, more preferably $Y^3$ is heptafluoroprop-2-yl or nonafluorobut-2-yl.

In one embodiment $Y^3$ is heptafluoroprop-2-yl.

In one embodiment $Y^3$ is nonafluorobut-2-yl.

Preferably $Y^4$ is hydrogen, chloro, fluoro or methyl.

Most preferably $Y^4$ is hydrogen.

Preferably $Y^5$ is cyano, halogen, methyl, ethyl or trifluoromethyl.

More preferably $Y^5$ is cyano, bromo, chloro, methyl, ethyl or trifluoromethyl.

Even more preferably $Y^5$ is bromo, chloro, methyl or ethyl.

Yet even more preferably $Y^5$ is bromo, methyl or ethyl.

Even more preferably $Y^5$ is methyl or ethyl.

Most preferably $Y^5$ is methyl.

Preferably $Y^6$ is cyano, halogen, methyl, ethyl, trifluoromethyl or methoxymethyl.

More preferably $Y^6$ is cyano, bromo, chloro, methyl, ethyl, trifluoromethyl or methoxymethyl.

Even more preferably $Y^6$ is bromo, chloro, methyl, ethyl or methoxymethyl.

Yet even more preferably $Y^6$ is bromo, methyl or ethyl.

Even more preferably $Y^6$ is methyl or ethyl.

Most preferably $Y^6$ is methyl.

Preferably $Y^7$ is hydrogen, chloro, fluoro or methyl.

Most preferably $Y^7$ is hydrogen.

Preferably $Y^8$ is heptafluoropropyl, heptafluoroprop-2-yl, heptafluoropropylthio, heptafluoropropylsulfinyl, heptafluoropropylsulfonyl, heptafluoroprop-2-ylthio, heptafluoroprop-2-ylsulfinyl, heptafluoroprop-2-ylsulfonyl or nonafluorobut-2-yl.

In one embodiment $Y^8$ is $C_2$-$C_6$perfluoroalkyl, more preferably $Y^8$ is heptafluoroprop-2-yl or nonafluorobut-2-yl.

In one embodiment $Y^8$ is heptafluoroprop-2-yl.

In one embodiment $Y^8$ is nonafluorobut-2-yl.

Preferably $Y^9$ is cyano, halogen, methyl, ethyl, trifluoromethyl or methoxymethyl.

More preferably $Y^9$ is cyano, bromo, chloro, methyl, ethyl, trifluoromethyl or methoxymethyl.

Even more preferably $Y^9$ is bromo, chloro, methyl, ethyl or methoxymethyl.

Yet even more preferably $Y^9$ is bromo, methyl or ethyl.

Even more preferably $Y^9$ is methyl or ethyl.

Most preferably $Y^9$ is methyl.

A preferred embodiment are compounds of formula (Ia) wherein $A^1$ is C—CN, and $A^2$, $A^3$, $A^4$ are CH.

A preferred embodiment are compounds of formula (Ib) wherein $A^2$ is C—CN, and $A^1$, $A^3$, and $A^4$ are CH.

A preferred embodiment are compounds of formula (Ic) wherein $A^3$ is C—CN, and $A^1$, $A^2$, and $A^4$ are CH.

A preferred embodiment are compounds of formula (Id) wherein $A^4$ is C—CN, and $A^1$, $A^2$, and $A^3$ are CH.

In a preferred embodiment $Q^2$ is 2,6-dimethyl-4-(heptafluoroprop-2-yl)-phenyl.

In a preferred embodiment $Q^2$ is 2-ethyl-6-methyl-4-(heptafluoroprop-2-yl)-phenyl.

In a preferred embodiment $Q^2$ is 2,6-diethyl-4-(heptafluoroprop-2-yl)-phenyl.

In a preferred embodiment $Q^2$ is 2-methoxymethyl-6-methyl-4-(heptafluoroprop-2-yl)-phenyl.

In a preferred embodiment $Q^2$ is 2-bromo-6-methyl-4-(heptafluoroprop-2-yl)-phenyl.

In a preferred embodiment $Q^2$ is 2-bromo-6-ethyl-4-(heptafluoroprop-2-yl)-phenyl.

In a preferred embodiment $Q^2$ is 2,6-dichloro-4-(heptafluoroprop-2-yl)-phenyl.

In a preferred embodiment $Q^2$ is 2,6-dibromo-4-(heptafluoroprop-2-yl)-phenyl.

In a preferred embodiment $Q^2$ is 2,6-dimethyl-4-(nonafluorobut-2-yl)-phenyl.

In a preferred embodiment $Q^2$ is 2-ethyl-6-methyl-4-(nonafluorobut-2-yl)-phenyl.

In a preferred embodiment $Q^2$ is 2,6-diethyl-4-(nonafluorobut-2-yl)-phenyl.

In a preferred embodiment $Q^2$ is 2-methoxymethyl-6-methyl-4-(nonafluorobut-2-yl)-phenyl.

In a preferred embodiment $Q^2$ is 2-bromo-6-methyl-4-(nonafluorobut-2-yl)-phenyl.

In a preferred embodiment $Q^2$ is 2-bromo-6-ethyl-4-(nonafluorobut-2-yl)-phenyl.

In a preferred embodiment $Q^2$ is 2,6-dichloro-4-(nonafluorobut-2-yl)-phenyl.

In a preferred embodiment $Q^2$ is 2,6-dibromo-4-(nonafluorobut-2-yl)-phenyl.

In one embodiment of the invention $R^2$ and $R^3$ are independently of each other hydrogen, $C_1$-$C_4$alkyl, or $C_1$-$C_4$alkylcarbonyl. The preferences for $R^2$ and $R^3$ are the same as set out for compounds of formula (I) except that $R^2$ and $R^3$ cannot be allyl, propargyl, hydroxy, acetyloxy or benzoyloxy.

In one embodiment of the invention each $R^5$ is independently hydrogen, halogen, $C_1$-$C_4$alkyl or trifluoromethyl. The preferences for $R^5$ are the same as set out for compounds of formula (I) except that $R^5$ cannot be methoxy.

In one embodiment of the invention $Y^1$, $Y^2$, $Y_4$ and $Y^5$ are independently of each other hydrogen, halogen, $C_1$-$C_6$alkyl, $C_1$-$C_6$haloalkyl, $C_1$-$C_6$alkoxy, $C_1$-$C_6$haloalkoxy, $C_1$-$C_6$alkylthio, $C_1$-$C_6$haloalkylthio, $C_1$-$C_6$alkylsulfinyl, $C_1$-$C_6$haloalkylsulfinyl, $C_1$-$C_6$alkyl-sulfonyl, $C_1$-$C_6$haloalkylsulfonyl, pentafluorosulfanyl, cyano, or nitro, provided that no more than one of $Y^1$ and $Y^5$ is hydrogen. The preferences for $Y^1$, $Y^2$, $Y^4$ and $Y^5$ are the same as set out for compounds of formula (I) except that $Y^1$ cannot be methoxymethyl.

In one embodiment of the invention $Y^6$, $Y^7$ and $Y^9$ are independently of each other hydrogen, $C_1$-$C_6$alkyl, $C_1$-$C_6$haloalkyl, $C_1$-$C_6$alkoxy, $C_1$-$C_6$haloalkoxy, $C_1$-$C_6$alkylthio, $C_1$-$C_6$haloalkylthio, $C_1$-$C_6$alkylsulfinyl, $C_1$-$C_6$haloalkylsulfinyl, $C_1$-$C_6$alkylsulfonyl, $C_1$-$C_6$haloalkylsulfonyl, pentafluorosulfanyl, cyano, or nitro, provided that no more than one of $Y^6$ and $Y^9$ is hydrogen. The preferences for $Y^6$, $Y^7$ and $Y^9$ are the same as set out for compounds of formula (I) except that $Y^6$ cannot be methoxymethyl.

The compounds in Tables 1 to 35 below illustrate the compounds of the invention.

Table 1:

Table 1 provides 24 compounds of formula (Ia) wherein Q is 2,6-dimethyl-4-(heptafluoro-prop-2-yl)-phenyl and $R^1$ has the values listed in the table below.

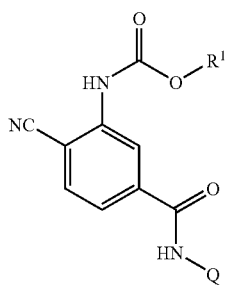

(Ia)

| Compound numbers | R¹ |
|---|---|
| 1.01 | methyl |
| 1.02 | ethyl |
| 1.03 | 2-fluoro-ethyl |
| 1.04 | 2-chloro-ethyl |
| 1.05 | 2-bromo-ethyl |
| 1.06 | 2-iodo-ethyl |
| 1.07 | 2-cyano-ethyl |
| 1.08 | 2,2-difluoro-ethyl |
| 1.09 | 2,2-dichloro-ethyl |
| 1.10 | 2,2,2-trifluoro-ethyl |
| 1.11 | 2,2,2-trichloro-ethyl |
| 1.12 | 2,2,2-tribromo-ethyl |
| 1.13 | n-propyl |
| 1.14 | 3-fluoro-propyl |
| 1.15 | 3-chloro-propyl |
| 1.16 | 3-bromo-propyl |
| 1.17 | 1,2-difluoro-prop-2-yl |
| 1.18 | 1,3-difluoro-prop-2-yl |
| 1.19 | 1,3-dichloro-prop-2-yl |
| 1.20 | 1-chloro-3-fluoro-prop-2-yl |
| 1.21 | 3,3,3-trifluoro-propyl |
| 1.22 | n-butyl |
| 1.23 | 4,4,4-trifluoro-butyl |
| 1.24 | Vinyl |

Table 2:
Table 2 provides 24 compounds of formula (Ia) wherein Q is 2-ethyl-6-methyl-4-(hepta-fluoroprop-2-yl)-phenyl and R¹ has the values listed in Table 1.
Table 3:
Table 3 provides 24 compounds of formula (Ia) wherein Q is 2,6-diethyl-4-(heptafluoroprop-2-yl)-phenyl and R¹ has the values listed in Table 1.
Table 4:
Table 4 provides 24 compounds of formula (Ia) wherein Q is 2-methoxymethyl-6-methyl-4-(heptafluoroprop-2-yl)-phenyl and R¹ has the values listed in Table 1.
Table 5:
Table 5 provides 24 compounds of formula (Ia) wherein Q is 2-bromo-6-methyl-4-(hepta-fluoroprop-2-yl)-phenyl and R¹ has the values listed in Table 1.
Table 6:
Table 6 provides 24 compounds of formula (Ia) wherein Q is 2-bromo-6-ethyl-4-(hepta-fluoroprop-2-yl)-phenyl and R¹ has the values listed in Table 1.
Table 7:
Table 7 provides 24 compounds of formula (Ia) wherein Q is 2,6-dichloro-4-(heptafluoro-prop-2-yl)-phenyl and R¹ has the values listed in Table 1.
Table 8:
Table 8 provides 24 compounds of formula (Ia) wherein Q is 2,6-dibromo-4-(heptafluoro-prop-2-yl)-phenyl and R¹ has the values listed in Table 1.

Table 9:
Table 9 provides 24 compounds of formula (Ia) wherein Q is 2,6-dimethyl-4-(nonafluorobut-2-yl)-phenyl and R¹ has the values listed in Table 1.
Table 10:
Table 10 provides 24 compounds of formula (Ia) wherein Q is 2-ethyl-6-methyl-4-(nona-fluorobut-2-yl)-phenyl and R¹ has the values listed in Table 1.
Table 11:
Table 11 provides 24 compounds of formula (Ia) wherein Q is 2,6-diethyl-4-(nonafluorobut-2-yl)-phenyl and R¹ has the values listed in Table 1.
Table 12:
Table 12 provides 24 compounds of formula (Ia) wherein Q is 2-methoxymethyl-6-methyl-4-(nonafluorobut-2-yl)-phenyl and R¹ has the values listed in Table 1.
Table 13:
Table 13 provides 24 compounds of formula (Ia) wherein Q is 2-bromo-6-methyl-4-(nona-fluorobut-2-yl)-phenyl and R¹ has the values listed in Table 1.
Table 14:
Table 14 provides 24 compounds of formula (Ia) wherein Q is 2-bromo-6-ethyl-4-(nona-fluorobut-2-yl)-phenyl and R¹ has the values listed in Table 1.
Table 15:
Table 15 provides 24 compounds of formula (Ia) wherein Q is 2,6-dichloro-4-(nonafluoro-but-2-yl)-phenyl and R¹ has the values listed in Table 1.
Table 16:
Table 16 provides 24 compounds of formula (Ia) wherein Q is 2,6-dibromo-4-(nonafluoro-but-2-yl)-phenyl and R¹ has the values listed in Table 1.
Table 17:
Table 17 provides 24 compounds of formula (Ia') wherein Q is 2,6-dimethyl-4-(heptafluoro-prop-2-yl)-phenyl and R¹ has the values listed in Table 1.

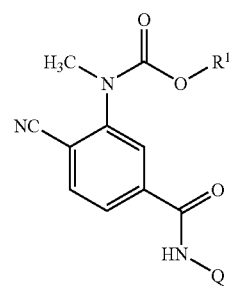

(Ia')

Table 18:
Table 18 provides 24 compounds of formula (Ia') wherein Q is 2-ethyl-6-methyl-4-(hepta-fluoroprop-2-yl)-phenyl and R¹ has the values listed in Table 1.
Table 19:
Table 19 provides 24 compounds of formula (Ia') wherein Q is 2,6-diethyl-4-(heptafluoro-prop-2-yl)-phenyl and R¹ has the values listed in Table 1.
Table 20:
Table 20 provides 24 compounds of formula (Ia') wherein Q is 2-methoxymethyl-6-methyl-4-(heptafluoroprop-2-yl)-phenyl and R¹ has the values listed in Table 1.
Table 21:
Table 21 provides 24 compounds of formula (Ia') wherein Q is 2-bromo-6-methyl-4-(hepta-fluoroprop-2-yl)-phenyl and R¹ has the values listed in Table 1.

Table 22:
Table 22 provides 24 compounds of formula (Ia') wherein Q is 2-bromo-6-ethyl-4-(hepta-fluoroprop-2-yl)-phenyl and $R^1$ has the values listed in Table 1.

Table 23:
Table 23 provides 24 compounds of formula (Ia') wherein Q is 2,6-dichloro-4-(heptafluoro-prop-2-yl)-phenyl and $R^1$ has the values listed in Table 1.

Table 24:
Table 24 provides 24 compounds of formula (Ia') wherein Q is 2,6-dibromo-4-(heptafluoro-prop-2-yl)-phenyl and $R^1$ has the values listed in Table 1.

Table 25:
Table 25 provides 24 compounds of formula (Ia') wherein Q is 2,6-dimethyl-4-(nonafluoro-but-2-yl)-phenyl and $R^1$ has the values listed in Table 1.

Table 26:
Table 26 provides 24 compounds of formula (Ia') wherein Q is 2-ethyl-6-methyl-4-(nona-fluorobut-2-yl)-phenyl and $R^1$ has the values listed in Table 1.

Table 27:
Table 27 provides 24 compounds of formula (Ia') wherein Q is 2,6-diethyl-4-(nonafluorobut-2-yl)-phenyl and $R^1$ has the values listed in Table 1.

Table 28:
Table 28 provides 24 compounds of formula (Ia') wherein Q is 2-methoxymethyl-6-methyl-4-(nonafluorobut-2-yl)-phenyl and $R^1$ has the values listed in Table 1.

Table 29:
Table 29 provides 24 compounds of formula (Ia') wherein Q is 2-bromo-6-methyl-4-(nona-fluorobut-2-yl)-phenyl and $R^1$ has the values listed in Table 1.

Table 30:
Table 30 provides 24 compounds of formula (Ia') wherein Q is 2-bromo-6-ethyl-4-(nona-fluorobut-2-yl)-phenyl and $R^1$ has the values listed in Table 1.

Table 31:
Table 31 provides 24 compounds of formula (Ia') wherein Q is 2,6-dichloro-4-(nonafluoro-but-2-yl)-phenyl and R' has the values listed in Table 1.

Table 32:
Table 32 provides 24 compounds of formula (Ia') wherein Q is 2,6-dibromo-4-(nonafluoro-but-2-yl)-phenyl and $R^1$ has the values listed in Table 1.

Table 33:
Table 33 provides 24 compounds of formula (Ib) wherein Q is 2,6-dimethyl-4-(heptafluoro-prop-2-yl)-phenyl and $R^1$ has the values listed in Table 1.

(Ib)

Table 34:
Table 34 provides 24 compounds of formula (Ic) wherein Q is 2,6-dimethyl-4-(heptafluoro-prop-2-yl)-phenyl and $R^1$ has the values listed in Table 1.

(Ic)

Table 35:
Table 35 provides 24 compounds of formula (Id) wherein Q is 2,6-dimethyl-4-(heptafluoro-prop-2-yl)-phenyl and $R^1$ has the values listed in Table 1.

(Id)

The compounds of the invention may be made by a variety of methods.

1) Compounds of formula (I), wherein $G^1$, $G^2$ and $G^3$ are oxygen, may be made by treatment of a compound of formula (II), wherein $G^3$ is oxygen, with a chloroformate of formula $R^1$—OCOCl.

Such reactions are usually carried out under basic conditions (for example in the presence of pyridine, triethylamine, 4-(dimethylamino)-pyridine or diisopropylethylamine), optionally in the presence of a nucleophilic catalyst such as hydroxybenzotriazole. Alternatively, it is possible to conduct the reaction in a biphasic system comprising an organic solvent, preferably ethyl acetate, and an aqueous solvent, preferably a solution of sodium hydrogen carbonate. Many chloroformates are commercially available. Alternatively, a dicarbonic acid diester, $(R^1—OCO)_2O$, or a 1-[(methoxycarbonyl)oxy]-succinimide, $R^1$—OCO-succinimide, can be used instead of the chloroformate $R^1$—OCOCl.

2) Compounds of formula (II), wherein $G^3$ is oxygen, may be made by treatment of compounds of formula (III) wherein R is OH, $C_1$-$C_6$alkoxy or Cl, F or Br with an amine of formula $NHR^3Q$.

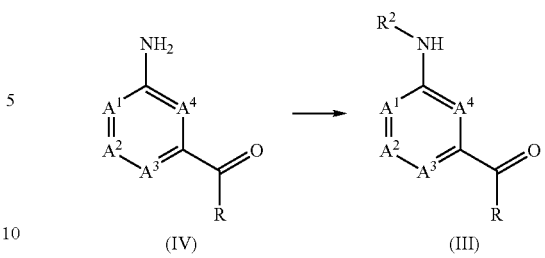

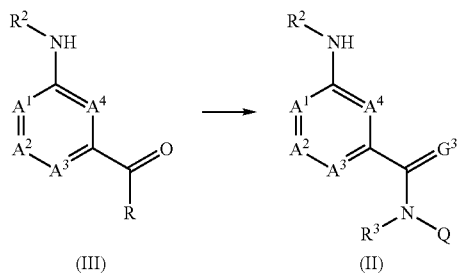

When R is OH such reactions are usually carried out in the presence of a coupling reagent, such as DCC (N,N'-dicyclohexylcarbodiimide), EDC (1-ethyl-3-[3-dimethylamino-propyl]-carbodiimide hydrochloride) or BOP-Cl (bis(2-oxo-3-oxazolidinyl)phosphonic chloride), in the presence of a base, such as pyridine, triethylamine, 4-(dimethylamino)-pyridine or diisopropylethylamine, and optionally in the presence of a nucleophilic catalyst, such as hydroxybenzotriazole. When R is Cl, such reactions are usually carried out under basic conditions (for example in the presence of pyridine, triethylamine, 4-(dimethylamino)-pyridine or diisopropylethylamine), again optionally in the presence of a nucleophilic catalyst. Alternatively, it is possible to conduct the reaction in a biphasic system comprising an organic solvent, preferably ethyl acetate, and an aqueous solvent, preferably a solution of sodium hydrogen carbonate. Also it is possible to conduct the reaction only with the substrate and the reagent in a suitable solvent, such as tetrahydrofuran. When R is $C_1$-$C_6$alkoxy it is sometimes possible to convert the ester directly to the amide by heating the ester and amine together in a thermal process.

3) Acid halides of formula (III), wherein $G^1$ is oxygen and R is Cl, F or Br, may be made from carboxylic acids of formula (III), wherein $G^1$ is oxygen and R is OH, under standard conditions, such as treatment with thionyl chloride or oxalyl chloride.

4) Carboxylic acids of formula (III), wherein $G^1$ is oxygen and R is OH, may be formed from esters of formula (III), wherein $G^1$ is oxygen and R is $C_1$-$C_6$alkoxy. It is known to a person skilled in the art that there are many methods for the hydrolysis of such esters depending on the nature of the alkoxy group. One widely used method to achieve such a transformation is the treatment of the ester with an alkali hydroxide, such as sodium hydroxide, in a solvent, such as ethanol and/or water.

5) Compounds of formula (III), wherein R is $C_1$-$C_6$alkoxy, may be made from compounds of formula (N) by sequential treatment with an alcohol of formula $R^2$—OH under acidic conditions and then formation of the N—$R^2$ bond. It is known to a person skilled in the art that there are many reported methods for the formation of this bond depending on the nature of the substituent $R^2$.

Alternatively, reactions based on oxidized versions of the alcohol such as the corresponding aldehyde and ketone or based on more activated analogues of the alcohols such as the corresponding halide or sulfonate may be used. For example, reductive amination may be achieved by treatment of the amine with an aldehyde or ketone and a reducing agent such as sodium cyanoborohydride or sodium borohydride. Alternatively alkylation may be achieved by treating the amine with an alkylating agent such as an alkyl halide, optionally in the presence of a base. Alternatively, arylation may be achieved by treatment of the amine with an aryl halide or sulfonate in the presence of a suitable catalyst/ligand system, often a palladium (0) complex. Compounds of formula (IV) and alcohols of formula $R^2$—OH are either known compounds or may be made by methods known to a person skilled in the art.

6) Compounds of formula (I), wherein $G^1$ and $G^3$ are sulfur and $G^2$ is oxygen, may be made from a compound of formula (I), wherein $G^1$, $G^2$ and $G^3$ are oxygen, by treatment with a thio-transfer reagent, such as Lawesson's reagent or phosphorus pentasulfide.

7) An alternative synthesis of compounds of formula (II), wherein $G^3$ is oxygen and $R^2$ is hydrogen, may be achieved by the reduction of nitro compounds of formula (VI), wherein $G^3$ is oxygen.

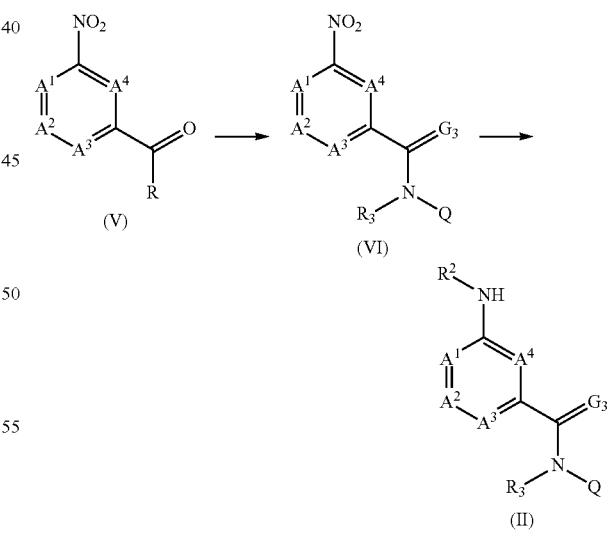

There are numerous methods for achieving such a transformation reported in the literature such as treatment with tin chloride under acidic conditions, or hydrogenation catalysed by a noble metal such as palladium on carbon.

8) Compounds of formula (VI), wherein $G^3$ is oxygen, may be derived from compounds of formula (V) wherein R is OH, $C_1$-$C_6$alkoxy or Cl, F or Br with an amine of formula $NHR^3Q$ under the standard conditions as described in 2). Compounds of formula (V) are either known or may be made by methods known to a person skilled in the art.

9) Compounds of formula (I), wherein $G^3$ is sulfur and $G^1$ and $G^2$ are oxygen, may be made by treatment of compounds of formula (II), wherein $G^3$ is oxygen, with a thio-transfer reagent such as Lawesson's reagent or phosphorus pentasulfide prior to elaborating to compounds of formula (I), wherein $G^3$ is sulfur and $G^1$ and $G^2$ are oxygen, as described in 1).

10) Compounds of formula (I), wherein $G^1$ is oxygen or sulfur, $G^2$ and $G^3$ are oxygen and $R^2$ is hydrogen, may be made by treatment of a compound of formula (VII), wherein $G^1$ is oxygen or sulfur, with an alcohol of formula $R^1$—OH.

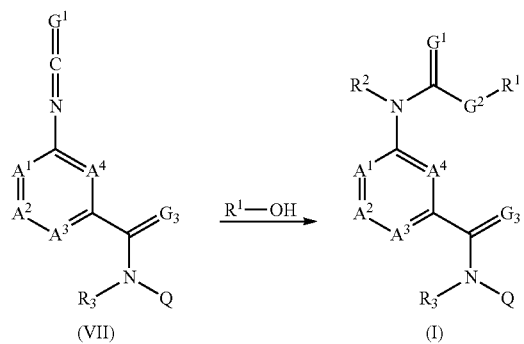

(VII)    (I)

Such reactions are usually carried out either in the alcohol itself as the solvent or in an inert solvent such as dichloromethane, tetrahydrofuran or toluene, optionally in the presence of a basic catalyst (for example in the presence of pyridine, triethylamine, 4-(dimethylamino)-pyridine or diisopropylethylamine).

11) Compounds of formula (I), wherein $G^1$ is oxygen or sulfur, $G^2$ is sulfur, $G^3$ is oxygen and $R^2$ is hydrogen, may be made by treatment of a compound of formula (VII), wherein $G^1$ is oxygen or sulfur, with an mercaptan of formula $R^1$—SH.

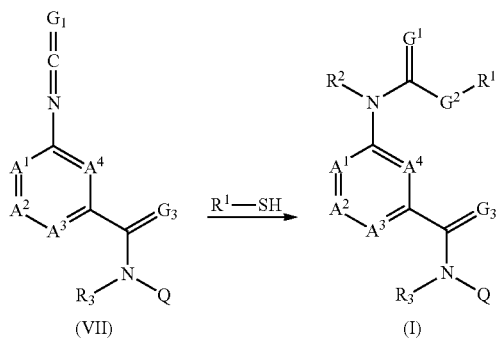

(VII)    (I)

Such reactions are usually carried out in an inert solvent such as dichloromethane, tetrahydrofuran or toluene, optionally in the presence of a basic catalyst (for example in the presence of pyridine, triethylamine, 4-(dimethylamino)-pyridine or diisopropylethylamine).

12) Compounds of formula (I), wherein $G^1$ is oxygen or sulfur, $G^2$ and $G^3$ are oxygen and $R^2$ is hydrogen, may be made by treatment of a compound of formula (IX) wherein $G^1$ is oxygen or sulfur, $G^2$ is oxygen, $R^2$ is hydrogen and R is OH, $C_1$-$C_6$alkoxy or Cl, F or Br with an amine of formula $NHR^3Q$ under the standard conditions as described in 2).

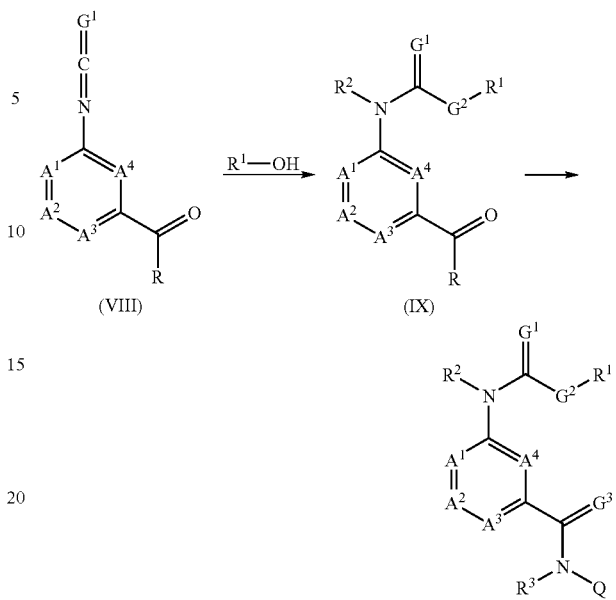

(VIII)    (IX)

(I)

Compounds of formula (IX), wherein $G^1$ is oxygen or sulfur, $G^2$ is oxygen and $R^2$ is hydrogen, may be made from compounds of formula (VIII) by reaction with alcohols of formula $R^1$—OH as described in 10).

13) Compounds of formula (VII), wherein $G^1$ is oxygen or sulfur, may be made by treatment of a compound of formula (II), wherein $R^2$ is hydrogen, with phosgene or oxalyl chloride for compounds of formula (VII), wherein $G^1$ is oxygen, or with thiophosgene, for compounds of formula (VII), wherein $G^1$ is sulfur.

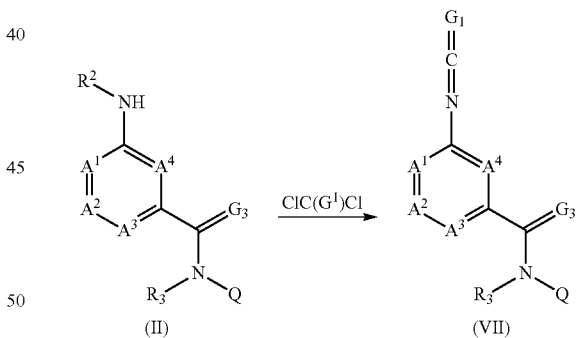

(II)    (VII)

Such reactions are usually carried out either an inert solvent such as dichloromethane or toluene, or in a biphasic system of water and the inert solvent optionally in the presence of a basic catalyst (for example in the presence of pyridine, triethylamine, 4-(dimethylamino)-pyridine or diisopropylethylamine or a carbonate, such as calcium carbonate or sodium hydrogen carbonate). Similarly compounds of formula (VIII), wherein $G^1$ is oxygen or sulfur, may be made from compounds of formula (IV).

14) Compounds of formula (V) wherein $R^4$ is cyano, can be made from a compound of formula (V') wherein LG is halogen, such as fluorine or chlorine, by reaction with a cyanide salt, such as potassium cyanide, optionally in the presence of a base, such as potassium carbonate.

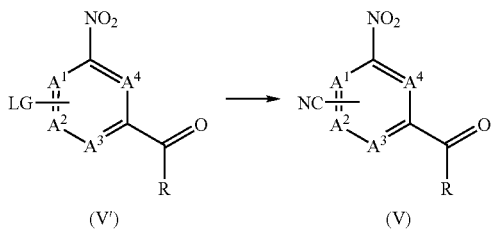

The displacement of a halogen with cyanide can also be carried out on intermediates of formula (VI). In both instances the presence of the nitro group facilitates the displacement of the leaving group by the cyanide ion. Likewise compounds (V) or (VI) wherein $R^4$ is thiocyanato, can be made from a compound of formula (V') or (VI') wherein LG is halogen, such as iodine, fluorine or chlorine, by reaction with a thiocyanato salt, such as potassium thiocyanate or copper thiocyanate as described for example in Journal of the Chemical Society, Chemical Communications, (2), 81-2; 1989 or Synthetic Communications, 10(8), 633-6; 1980.

15) Compounds of formula (V) wherein $R^4$ is cyano, can be made, for example, from a compound of formula (V') wherein LG is an amine, by reaction with a cyanide salt, such as copper cyanide, via a diazotisation reaction. The displacement of an amine with cyanide can also be carried out on intermediates of formula (VI).

16) Compounds of formula (I) wherein $R^4$ is cyano, can be prepared, for example, from a compound of formula (II), (III), (IV), (V), (I), (IX), (V') which have a halogen in the central ring by reaction with a metal cyanide, such as cuprous cyanide, zinc cyanide, or potassium cyanide, optionally in the presence of a suitable palladium catalyst, such as tetrakis(triphenylphosphine)palladium, and optionally in the presence of a metal halide, such as cuprous iodide, or zinc iodide, in suitable solvent such N,N-dimethylformamide or N-methylpyrrolidine. Such processes are described, for example in Organic Process Research & Development (2006), 10(3), 553-555, Synlett (2006), (1), 65-68, Journal of Medicinal Chemistry (2004), 47(8), 1969, Synthetic Communications (1994), 24(6), 887-90, Tetrahedron (2001), 57(8), 1581 and WO 2004067528.

16) Compounds of formula (II), wherein $G^1$ and $G^2$ are oxygen and $R^4$ is thiocyanato, can be made, for example, by treatment of a compound of formula (H) wherein $R^2$ is hydrogen and $R^4$ is hydrogen with a thiocyanate salt in the presence of halogen or a halogen equivalent (N-chlorosuccinimide, N-bromosuccinimide) as described, for example, in Pest Management Science, 59(1), 25-35; 2003 or Inorganic Chemistry, 44(6), 1837-1845; 2005.

17) Compounds of formula (I), wherein $G^1$ and $G^2$ are oxygen and $R^4$ is amino-thiocarbonyl, can be made, for example, by treatment of a compound of formula (V) or (VI), wherein $R^4$ is cyano with $P_4S_{10}$ or $H_2S$ as described, for example, in Journal of Fluorine Chemistry (2006), 127(1), 63-67, and Synthesis (2006), (2), 224-226 or Synthetic Communications (2003), 33(24), 4279-4284. Alternatively, compounds of formula (I), wherein $G^1$ and $G^2$ are oxygen and $R^4$ is aminothiocarbonyl can be made, for example, by treatment of a compound of formula (I), wherein $R^4$ is cyano by reaction with sodium hydrogen sulfide and magnesium chloride as described, for example, in Synthetic Communications (2005), 35(5), 761-764.

18) Compounds of formula (I), wherein $G^1$ and $G^2$ are oxygen and $R^4$ is N—$C_1$-$C_4$alkyl-aminothiocarbonyl or N,N-di-$C_1$-$C_4$alkyl-aminothiocarbonyl, can be made, for example, by treatment of a compound of formula (I), wherein $R^4$ is aminothiocarbonyl by reaction with electrophile as described, for example, in Tetrahedron Letters (1988), 29(15), 1755-8 or, for example, by treatment of a compound of formula (I), wherein $R^4$ is amino-carbonyl with electrophile as described, for example, in Tetrahedron Letters (2000), 41(25), 4933, Journal of Medicinal Chemistry (1975), 18(9), 926, Chemical Communications (Cambridge, United Kingdom) (2006), (23), 2483, Organometallics (2004), 23(8), 1.649-1651, Tetrahedron Letters (1994), 35(20), 3313-14, Bulletin of the Chemical Society of Japan (1985), 58(3), 838-43 followed by treatment with a thiotransfer reagent such as Lawesson's reagent or phosphorus pentasulfide.

The compounds of formula (I) can be used to combat and control infestations of insect pests such as Lepidoptera, Diptera, Hemiptera, Thysanoptera, Orthoptera, Dictyoptera, Coleoptera, Siphonaptera, Hymenoptera and Isoptera and also other invertebrate pests, for example, acarine, nematode and mollusc pests. Insects, acarines, nematodes and molluscs are hereinafter collectively referred to as pests. The pests which may be combated and controlled by the use of the invention compounds include those pests associated with agriculture (which term includes the growing of crops for food and fibre products), horticulture and animal husbandry, companion animals, forestry and the storage of products of vegetable origin (such as fruit, grain and timber); those pests associated with the damage of man-made structures and the transmission of diseases of man and animals; and also nuisance pests (such as flies).

Examples of pest species which may be controlled by the compounds of formula (I) include: *Myzus persicae* (aphid), *Aphis gossypii* (aphid), *Aphis fabae* (aphid), *Lygus* spp. (capsids), *Dysdercus* spp. (capsids), *Nilaparvata lugens* (planthopper), *Nephotettixc incticeps* (leafhopper), *Nezara* spp. (stinkbugs), *Euschistus* spp. (stinkbugs), *Leptocorisa* spp. (stinkbugs), *Frankliniella occidentalis* (thrip), *Thrips* spp. (thrips), *Leptinotarsa decemlineata* (Colorado potato beetle), *Anthonomus grandis* (boll weevil), *Aonidiella* spp. (scale insects), *Trialeurodes* spp. (white flies), *Bemisia tabaci* (white fly), *Ostrinia nubilalis* (European corn borer), *Spodoptera littoralis* (cotton leafworm), *Heliothis virescens* (tobacco budworm), *Helicoverpa armigera* (cotton bollworm), *Helicoverpa zea* (cotton bollworm), *Sylepta derogata* (cotton leaf roller), *Pieris brassicae* (white butterfly), *Plutella xylostella* (diamond back moth), *Agrotis* spp. (cutworms), *Chilo suppressalis* (rice stem borer), *Locusta migratoria* (locust), *Chortiocetes terminifera* (locust), *Diabrotica* spp. (rootworms), *Panonychus ulmi* (European red mite), *Panonychus citri* (citrus red mite), *Tetranychus urticae* (two-spotted spider mite), *Tetranychus cinnabarinus* (carmine spider mite), *Phyllocoptruta oleivora* (citrus rust mite), *Polyphagotarsonemus latus* (broad mite), *Brevipalpus* spp. (flat mites), *Boophilus microplus* (cattle tick), *Dermacentor variabilis* (American dog tick), *Ctenocephalides felis* (cat flea), *Liriomyza* spp. (leafminer), *Musca domestica* (housefly), *Aedes aegypti* (mosquito), *Anopheles* spp. (mosquitoes), *Culex* spp. (mosquitoes), *Lucillia* spp. (blowflies), *Blattella germanica* (cockroach), *Periplaneta americana* (cockroach), *Blatta orientalis* (cockroach), termites of the Mastotermitidae (for example *Mastotermes* spp.), the Kalotermitidae (for example *Neotermes* spp.), the Rhinotermitidae (for example *Coptotermes formosanus, Reticulitermes flavipes, R. speratu, R. virginicus, R. hesperus, and R. santonensis*) and the Termitidae (for example *Globitermes sulfureus*), *Solenopsis geminata* (fire ant), *Monomorium pharaonis* (pharaoh's ant), *Damalinia* spp. and *Linognathus* spp. (biting and sucking lice), *Meloidogyne* spp. (root knot nematodes), *Globodera* spp. and *Heterodera* spp. (cyst nematodes), *Pratylenchus* spp. (lesion nematodes), *Rhodopholus* spp. (banana burrowing nematodes), *Tylenchulus* spp. (citrus nematodes), *Haemonchus contortus* (barber pole worm), *Caenorhabditis elegans* (vinegar eelworm), *Trichostrongylus* spp. (gastro intestinal nematodes) and *Deroceras reticulatum* (slug).

The invention therefore provides a method of combating and controlling insects, acarines, nematodes or molluscs which comprises applying an insecticidally, acaricidally, nematicidally or molluscicidally effective amount of a compound of formula (I), or a composition containing a compound of formula (I), to a pest, a locus of pest, preferably a plant, or to a plant susceptible to attack by a pest, The compounds of formula (I) are preferably used against insects, acarines or nematodes.

The term "plant" as used herein includes seedlings, bushes and trees. In order to apply a compound of formula (I) as an insecticide, acaricide, nematicide or molluscicide to a pest, a locus of pest, or to a plant susceptible to attack by a pest, a compound of formula (I) is usually formulated into a composition which includes, in addition to the compound of formula (I), a suitable inert diluent or carrier and, optionally, a surface active agent (SFA). SFAs are chemicals which are able to modify the properties of an interface (for example, liquid/solid, liquid/air or liquid/liquid interfaces) by lowering the interfacial tension and thereby leading to changes in other properties (for example dispersion, emulsification and wetting). It is preferred that all compositions (both solid and liquid formulations) comprise, by weight, 0.0001 to 95%, more preferably 1 to 85%, for example 5 to 60%, of a compound of formula (I). The composition is generally used for the control of pests such that a compound of formula (I) is applied at a rate of from 0.1 g to 10 kg per hectare, preferably from 1 g to 6 kg per hectare, more preferably from 1 g to 1 kg per hectare.

When used in a seed dressing, a compound of formula (I) is used at a rate of 0.0001 g to 10 g (for example 0.001 g or 0.05 g), preferably 0.005 g to 10 g, more preferably 0.005 g to 4 g, per kilogram of seed.

In another aspect the present invention provides an insecticidal, acaricidal, nematicidal or molluscicidal composition comprising an insecticidally, acaricidally, nematicidally or molluscicidally effective amount of a compound of formula (I) and a suitable carrier or diluent therefor. The composition is preferably an insecticidal, acaricidal, nematicidal or molluscicidal composition.

The compositions can be chosen from a number of formulation types, including dustable powders (DP), soluble powders (SP), water soluble granules (SG), water dispersible granules (WG), wettable powders (WP), granules (GR) (slow or fast release), soluble concentrates (SL), oil miscible liquids (OL), ultra low volume liquids (UL), emulsifiable concentrates (EC), dispersible concentrates (DC), emulsions (both oil in water (EW) and water in oil (EO)), micro-emulsions (ME), suspension concentrates (SC), aerosols, fogging/smoke formulations, capsule suspensions (CS) and seed treatment formulations. The formulation type chosen in any instance will depend upon the particular purpose envisaged and the physical, chemical and biological properties of the compound of formula (I).

Dustable powders (DP) may be prepared by mixing a compound of formula (I) with one or more solid diluents (for example natural clays, kaolin, pyrophyllite, bentonite, alumina, montmorillonite, kieselguhr, chalk, diatomaceous earths, calcium phosphates, calcium and magnesium carbonates, sulfur, lime, flours, talc and other organic and inorganic solid carriers) and mechanically grinding the mixture to a fine powder.

Soluble powders (SP) may be prepared by mixing a compound of formula (I) with one or more water-soluble inorganic salts (such as sodium hydrogen carbonate, sodium carbonate or magnesium sulfate) or one or more water-soluble organic solids (such as a polysaccharide) and, optionally, one or more wetting agents, one or more dispersing agents or a mixture of said agents to improve water dispersibility/solubility. The mixture is then ground to a fine powder. Similar compositions may also be granulated to form water soluble granules (SG).

Wettable powders (WP) may be prepared by mixing a compound of formula (I) with one or more solid diluents or carriers, one or more wetting agents and, preferably, one or more dispersing agents and, optionally, one or more suspending agents to facilitate the dispersion in liquids. The mixture is then ground to a fine powder. Similar compositions may also be granulated to form water dispersible granules (WG).

Granules (GR) may be formed either by granulating a mixture of a compound of formula (I) and one or more powdered solid diluents or carriers, or from pre-formed blank granules by absorbing a compound of formula (I) (or a solution thereof, in a suitable agent) in a porous granular material (such as pumice, attapulgite clays, fuller's earth, kieselguhr, diatomaceous earths or ground corn cobs) or by adsorbing a compound of formula (I) (or a solution thereof, in a suitable agent) on to a hard core material (such as sands, silicates, mineral carbonates, sulfates or phosphates) and drying if necessary. Agents which are commonly used to aid absorption or adsorption include solvents (such as aliphatic and aromatic petroleum solvents, alcohols, ethers, ketones and esters) and sticking agents (such as polyvinyl acetates, polyvinyl alcohols, dextrins, sugars and vegetable oils). One or more other additives may also be included in granules (for example an emulsifying agent, wetting agent or dispersing agent).

Dispersible Concentrates (DC) may be prepared by dissolving a compound of formula (I) in water or an organic solvent, such as a ketone, alcohol or glycol ether. These solutions may contain a surface active agent (for example to improve water dilution or prevent crystallisation in a spray tank).

Emulsifiable concentrates (EC) or oil-in-water emulsions (EW) may be prepared by dissolving a compound of formula (I) in an organic solvent (optionally containing one or more wetting agents, one or more emulsifying agents or a mixture of said agents). Suitable organic solvents for use in ECs include aromatic hydrocarbons (such as alkylbenzenes or alkylnaphthalenes, exemplified by SOLVESSO 100, SOLVESSO 150 and SOLVESSO 200; SOLVESSO is a Registered Trade Mark), ketones (such as cyclohexanone or methylcyclohexanone) and alcohols (such as benzyl alcohol, furfuryl alcohol or butanol), N-alkylpyrrolidones (such as N-methylpyrrolidone or N-octylpyrrolidone), dimethyl amides of fatty acids (such as $C_8$-$C_{10}$ fatty acid dimethylamide) and chlorinated hydrocarbons. An EC product may spontaneously emulsify on addition to water, to produce an emulsion with sufficient stability to allow spray application through appropriate equipment. Preparation of an EW involves obtaining a compound of formula (I) either as a liquid (if it is not a liquid at ambient temperature, it may be melted at a reasonable temperature, typically below 70° C.) or in solution (by dissolving it in an appropriate solvent) and then emulsifiying the resultant liquid or solution into water containing one or more SFAs, under high shear, to produce an emulsion. Suitable solvents for use in EWs include vegetable oils, chlorinated hydrocarbons (such as chlorobenzenes), aromatic solvents (such as alkylbenzenes or alkylnaphthalenes) and other appropriate organic solvents which have a low solubility in water.

Microemulsions (ME) may be prepared by mixing water with a blend of one or more solvents with one or more SFAs, to produce spontaneously a thermodynamically stable isotropic liquid formulation. A compound of formula (I) is present initially in either the water or the solvent/SFA blend. Suitable solvents for use in MEs include those hereinbefore described for use in ECs or in EWs. An ME may be either an oil-in-water or a water-in-oil system (which system is present may be determined by conductivity measurements) and may be suitable for mixing water-soluble and oil-soluble pesticides in the same formulation. An ME is suitable for dilution into water, either remaining as a microemulsion or forming a conventional oil-in-water emulsion.

Suspension concentrates (SC) may comprise aqueous or non-aqueous suspensions of finely divided insoluble solid particles of a compound of formula (I). SCs may be prepared by ball or bead milling the solid compound of formula (I) in a suitable medium, optionally with one or more dispersing agents, to produce a fine particle suspension of the compound. One or more wetting agents may be included in the composition and a suspending agent may be included to reduce the rate at which the particles settle. Alternatively, a compound of formula (I) may be dry milled and added to water, containing agents hereinbefore described, to produce the desired end product.

Aerosol formulations comprise a compound of formula (I) and a suitable propellant (for example n-butane). A compound of formula (I) may also be dissolved or dispersed in a suitable medium (for example water or a water miscible liquid, such as n-propanol) to provide compositions for use in non-pressurised, hand-actuated spray pumps.

A compound of formula (I) may be mixed in the dry state with a pyrotechnic mixture to form a composition suitable for generating, in an enclosed space, a smoke containing the compound.

Capsule suspensions (CS) may be prepared in a manner similar to the preparation of EW formulations but with an additional polymerisation stage such that an aqueous dispersion of oil droplets is obtained, in which each oil droplet is encapsulated by a polymeric shell and contains a compound of formula (I) and, optionally, a carrier or diluent therefor. The polymeric shell may be produced by either an interfacial polycondensation reaction or by a coacervation procedure. The compositions may provide for controlled release of the compound of formula (I) and they may be used for seed treatment. A compound of formula (I) may also be formulated in a biodegradable polymeric matrix to provide a slow, controlled release of the compound.

A composition may include one or more additives to improve the biological performance of the composition (for example by improving wetting, retention or distribution on surfaces; resistance to rain on treated surfaces; or uptake or mobility of a compound of formula (I)). Such additives include surface active agents, spray additives based on oils, for example certain mineral oils or natural plant oils (such as soy bean and rape seed oil), and blends of these with other bio-enhancing adjuvants (ingredients which may aid or modify the action of a compound of formula (I)).

A compound of formula (I) may also be formulated for use as a seed treatment, for example as a powder composition, including a powder for dry seed treatment (DS), a water soluble powder (SS) or a water dispersible powder for slurry treatment (WS), or as a liquid composition, including a flowable concentrate (FS), a solution (LS) or a capsule suspension (CS). The preparations of DS, SS, WS, FS and LS compositions are very similar to those of, respectively, DP, SP, WP, SC and DC compositions described above. Compositions for treating seed may include an agent for assisting the adhesion of the composition to the seed (for example a mineral oil or a film-forming barrier).

Wetting agents, dispersing agents and emulsifying agents may be surface SFAs of the cationic, anionic, amphoteric or non-ionic type.

Suitable SFAs of the cationic type include quaternary ammonium compounds (for example cetyltrimethyl ammonium bromide), imidazolines and amine salts.

Suitable anionic SFAs include alkali metals salts of fatty acids, salts of aliphatic monoesters of sulfuric acid (for example sodium lauryl sulfate), salts of sulfonated aromatic compounds (for example sodium dodecylbenzenesulfonate, calcium dodecylbenzenesulfonate, butylnaphthalene sulfonate and mixtures of sodium di-isopropyl- and tri-isopropyl-naphthalene sulfonates), ether sulfates, alcohol ether sulfates (for example sodium laureth-3-sulfate), ether carboxylates (for example sodium laureth-3-carboxylate), phosphate esters (products from the reaction between one or more fatty alcohols and phosphoric acid (predominately mono-esters) or phosphorus pentoxide (predominately diesters), for example the reaction between lauryl alcohol and tetraphosphoric acid; additionally these products may be ethoxylated), sulfosuccinamates, paraffin or olefine sulfonates, taurates and lignosulfonates.

Suitable SFAs of the amphoteric type include betaines, propionates and glycinates.

Suitable SFAs of the non-ionic type include condensation products of alkylene oxides, such as ethylene oxide, propylene oxide, butylene oxide or mixtures thereof, with fatty alcohols (such as oleyl alcohol or cetyl alcohol) or with alkylphenols (such as octylphenol, nonylphenol or octylcresol); partial esters derived from long chain fatty acids or hexitol anhydrides; condensation products of said partial esters with ethylene oxide; block polymers (comprising ethylene oxide and propylene oxide); alkanolamides; simple esters (for example fatty acid polyethylene glycol esters); amine oxides (for example lauryl dimethyl amine oxide); and lecithins.

Suitable suspending agents include hydrophilic colloids (such as polysaccharides, polyvinylpyrrolidone or sodium carboxymethylcellulose) and swelling clays (such as bentonite or attapulgite).

A compound of formula (I) may be applied by any of the known means of applying pesticidal compounds. For example, it may be applied, formulated or unformulated, to the pests or to a locus of the pests (such as a habitat of the pests, or a growing plant liable to infestation by the pests) or to any part of the plant, including the foliage, stems, branches or roots, to the seed before it is planted or to other media in which plants are growing or are to be planted (such as soil surrounding the roots, the soil generally, paddy water or hydroponic culture systems), directly or it may be sprayed on, dusted on, applied by dipping, applied as a cream or paste formulation, applied as a vapour or applied through distribution or incorporation of a composition (such as a granular composition or a composition packed in a water-soluble bag) in soil or an aqueous environment.

A compound of formula (I) may also be injected into plants or sprayed onto vegetation using electrodynamic spraying techniques or other low volume methods, or applied by land or aerial irrigation systems.

Compositions for use as aqueous preparations (aqueous solutions or dispersions) are generally supplied in the form of a concentrate containing a high proportion of the active ingredient, the concentrate being added to water before use. These concentrates, which may include DCs, SCs, ECs, EWs, MEs, SGs, SPs, WPs, WGs and CSs, are often required to withstand storage for prolonged periods and, after such storage, to be capable of addition to water to form aqueous preparations which remain homogeneous for a sufficient time to enable them to be applied by conventional spray equipment. Such aqueous preparations may contain varying amounts of a compound of formula (I) (for example 0.0001 to 10%, by weight) depending upon the purpose for which they are to be used.

A compound of formula (I) may be used in mixtures with fertilisers (for example nitrogen-, potassium- or phosphorus-containing fertilisers). Suitable formulation types include granules of fertiliser. The mixtures suitably contain up to 25% by weight of the compound of formula (I).

The invention therefore also provides a fertiliser composition comprising a fertiliser and a compound of formula (I).

The compositions of this invention may contain other compounds having biological activity, for example micronutrients or compounds having fungicidal activity or which possess plant growth regulating, herbicidal, insecticidal, nematicidal or acaricidal activity.

The compound of formula (I) may be the sole active ingredient of the composition or it may be admixed with one or more additional active ingredients such as a pesticide, fungicide, synergist, herbicide or plant growth regulator where appropriate. An additional active ingredient may: provide a composition having a broader spectrum of activity or increased persistence at a locus; synergise the activity or complement the activity (for example by increasing the speed of effect or overcoming repellency) of the compound of formula (I); or help to overcome or prevent the development of resistance to individual components. The particular additional active ingredient will depend upon the intended utility of the composition. Examples of suitable pesticides include the following:

a) Pyrethroids, such as permethrin, cypermethrin, fenvalerate, esfenvalerate, deltamethrin, cyhalothrin (in particular lambda-cyhalothrin), bifenthrin, fenpropathrin, cyfluthrin, tefluthrin, fish safe pyrethroids (for example ethofenprox), natural pyrethrin, tetramethrin, s-bioallethrin, fenfluthrin, prallethrin or 5-benzyl-3-furylmethyl-(E)-(1R,3S)-2,2-dimethyl-3-(2-oxothiolan-3-ylidenemethyl)cyclopropane carboxylate;
b) Organophosphates, such as, profenofos, sulprofos, acephate, methyl parathion, azinphos-methyl, demeton-s-methyl, heptenophos, thiometon, fenamiphos, monocrotophos, profenofos, triazophos, methamidophos, dimethoate, phosphamidon, malathion, chlorpyrifos, phosalone, terbufos, fensulfothion, fonofos, phorate, phoxim, pirimiphos-methyl, pirimiphos-ethyl, fenitrothion, fosthiazate or diazinon;
c) Carbamates (including aryl carbamates), such as pirimicarb, triazamate, cloethocarb, carbofuran, furathiocarb, ethiofencarb, aldicarb, thiofurox, carbosulfan, bendiocarb, fenobucarb, propoxur, methomyl or oxamyl;
d) Benzoyl ureas, such as diflubenzuron, triflumuron, hexaflumuron, flufenoxuron or chlorfluazuron;
e) Organic tin compounds, such as cyhexatin, fenbutatin oxide or azocyclotin;
f) Pyrazoles, such as tebufenpyrad and fenpyroximate;
g) Macrolides, such as avermectins or milbemycins, for example abamectin, emamectin benzoate, ivermectin, milbemycin, spinosad or azadirachtin;
h) Hormones or pheromones;
i) Organochlorine compounds such as endosulfan, benzene hexachloride, DDT, chlordane or dieldrin;
j) Amidines, such as chlordimeform or amitraz;
k) Fumigant agents, such as chloropicrin, dichloropropane, methyl bromide or metam;
l) Neonicotinoid compounds such as imidacloprid, thiacloprid, acetamiprid, nitenpyram, dinotefuran or thiamethoxam;
m) Diacylhydrazines, such as tebufenozide, chromafenozide or methoxyfenozide;
n) Diphenyl ethers, such as diofenolan or pyriproxifen;
o) Indoxacarb;
p) Chlorfenapyr;
q) Pymetrozine;
r) Spirotetramat, Spirodiclofen or Spiromesifen; or
s) Flubendiamid or Rynaxypyr In addition to the major chemical classes of pesticide listed above, other pesticides having particular targets may be employed in the composition, if appropriate for the intended utility of the composition. For instance, selective insecticides for particular crops, for example stemborer specific insecticides (such as cartap) or hopper specific insecticides (such as buprofezin) for use in rice may be employed. Alternatively insecticides or acaricides specific for particular insect species/stages may also be included in the compositions (for example acaricidal ovo-larvicides, such as clofentezine, flubenzimine, hexythiazox or tetradifon; acaricidal motilicides, such as dicofol or propargite; acaricides, such as bromopropylate or chlorobenzilate; or growth regulators, such as hydramethylnon, cyromazine, methoprene, chlorfluazuron or diflubenzuron).

Examples of fungicidal compounds which may be included in the composition of the invention are (E)-N-methyl-2-[2-(2,5-dimethylphenoxymethyl)phenyl]-2-methoxyiminoacetamide (SSF-129), 4-bromo-2-cyano-N,N-dimethyl-6-trifluoromethylbenzimidazole-1-sulfonamide, α-[N-(3-chloro-2,6-xylyl)-2-methoxyacetamido]-γ-butyrolactone, 4-chloro-2-cyano-N,N-dimethyl-5-p-tolylimidazole-1-sulfonamide (IKF-916, cyamidazosulfamid), 3-5-dichloro-N-(3-chloro-1-ethyl-1-methyl-2-oxopropyl)-4-methylbenzamide (RH-7281, zoxamide), N-allyl-4,5,-dimethyl-2-trimethylsilylthiophene-3-carboxamide (MON65500), N-(1-cyano-1,2-dimethylpropyl)-2-(2,4-dichlorophenoxy) propionamide (AC382042), N-(2-methoxy-5-pyridyl)-cyclopropane carboxamide, acibenzolar (CGA245704), alanycarb, aldimorph, anilazine, azaconazole, azoxystrobin, benalaxyl, benomyl, biloxazol, bitertanol, blasticidin S, bromuconazole, bupirimate, captafol, captan, carbendazim, carbendazim chlorhydrate, carboxin, carpropamid, carvone, CGA41396, CGA41397, chinomethionate, chlorothalonil, chlorozolinate, clozylacon, copper containing compounds such as copper oxychloride, copper oxyquinolate, copper sulfate, copper tallate and Bordeaux mixture, cymoxanil, cyproconazole, cyprodinil, debacarb, di-2-pyridyl disulfide 1,1'-dioxide, dichlofluanid, diclomezine, dicloran, diethofencarb, difenoconazole, difenzoquat, diflumetorim, O,O-di-iso-propyl-S-benzyl thiophosphate, dimefluazole, dimetconazole, dimethomorph, dimethirimol, diniconazole, dinocap, dithianon, dodecyl dimethyl ammonium chloride, dodemorph, dodine, doguadine, edifenphos, epoxiconazole, ethirimol, ethyl(Z)—N-benzyl-N([methyl(methyl-thioethylideneaminooxycarbonyl)amino]thio)-β-alaninate, etridiazole, famoxadone, fenamidone (RPA407213), fenarimol, fenbuconazole, fenfuram, fenhexamid (KBR2738), fenpiclonil, fenpropidin, fenpropimorph, fentin acetate, fentin hydroxide, ferbam, ferimzone, fluazinam, fludioxonil, flumetover, fluoroimide, fluquinconazole, flusilazole, flutolanil, flutriafol, folpet, fuberidazole, furalaxyl, furametpyr, guazatine, hexaconazole, hydroxyisoxazole, hymexazole, imazalil, imibenconazole, iminoctadine, iminoctadine triacetate, ipconazole, iprobenfos, iprodione, iprovalicarb (SZX0722), isopropanyl butyl carbamate, isoprothiolane, kasugamycin, kresoxim-methyl, LY186054, LY211795, LY248908, mancozeb, maneb, mefenoxam, mepanipyrim, mepronil, metalaxyl, metconazole, metiram, metiram-zinc, metominostrobin, myclobutanil, neoasozin, nickel dimethyldithiocarbamate, nitrothal-isopropyl, nuarimol, ofurace, organomercury compounds, oxadixyl, oxasulfuron, oxolinic acid, oxpoconazole, oxycarboxin, pefurazoate, penconazole, pencycuron, phenazin oxide, phosetyl-A1, phosphorus acids, phthalide, picoxystrobin (ZA1963), polyoxin D, polyram, probenazole, prochloraz, procymidone, propamocarb, propiconazole, propineb, propionic acid, pyrazophos, pyrifenox, pyrimethanil, pyroquilon, pyroxyfur, pyrrolnitrin, quaternary ammonium compounds, quinomethionate, quinoxyfen, quintozene, sipconazole (F-155), sodium pentachlorophenate, spiroxamine, streptomycin, sulfur, tebuconazole, tecloftalam, tecnazene, tetraconazole, thiabendazole, thifluzamid, 2-(thiocyanomethylthio)benzothiazole, thiophanate-methyl, thiram, timibenconazole, tolclofos-methyl, tolylfluanid, triadimefon, triadimenol, triazbutil, triazoxide, tricyclazole, tridemorph, trifloxystrobin (CGA279202), triforine, triflumizole, triticonazole, validamycin A, vapam, vinclozolin, zineb and ziram.

The compounds of formula (I) may be mixed with soil, peat or other rooting media for the protection of plants against seed-borne, soil-borne or foliar fungal diseases.

Examples of suitable synergists for use in the compositions include piperonyl butoxide, sesamex, safroxan and dodecyl imidazole.

Suitable herbicides and plant-growth regulators for inclusion in the compositions will depend upon the intended target and the effect required.

An example of a rice selective herbicide which may be included is propanil. An example of a plant growth regulator for use in cotton is PIX™.

Some mixtures may comprise active ingredients which have significantly different physical, chemical or biological properties such that they do not easily lend themselves to the same conventional formulation type. In these circumstances other formulation types may be prepared. For example, where one active ingredient is a water insoluble solid and the other a water insoluble liquid, it may nevertheless be possible to disperse each active ingredient in the same continuous aqueous phase by dispersing the solid active ingredient as a suspension (using a preparation analogous to that of an SC) but dispersing the liquid active ingredient as an emulsion (using a preparation analogous to that of an EW). The resultant composition is a suspoemulsion (SE) formulation.

The following Examples illustrate, but do not limit, the invention.

PREPARATION EXAMPLES

Example I1

Preparation of 4-cyano-N[2,6-dimethyl-4-(1,2,2,2-tetrafluoro-1-trifluoromethyl-ethyl)-phenyl]-3-nitro-benzamide

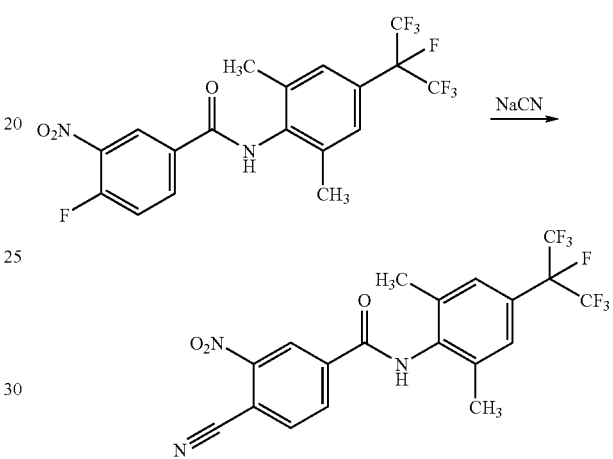

To a solution of N[2,6-dimethyl-4-(1,2,2,2-tetrafluoro-1-trifluoromethyl-ethyl)-phenyl]-4-fluoro-3-nitro-benzamide (2.008 g, 4.4 mmol) (prepared according to WO 05/073165) in N,N-dimethylformamide (25 ml) was added sodium cyanide (0.237 g, 4.84 mmol). The reaction mixture was stirred at ambient temperature for 48 hours. Then water (20 ml) was added and the organic phase extracted three times with ethyl acetate (3×100 ml). The combined organic extracts were washed with water and brine, dried over sodium sulfate and concentrated. The residue was purified by column chromatography on silica gel (eluent: cyclohexane/ethyl acetate 1:4) to give 4-cyano-N-[2,6-dimethyl-4-(1,2,2,2-tetrafluoro-1-trifluoromethyl-ethyl)-phenyl]-3-nitro-benzamide (1.0 g, 49% yield). $^1$H-NMR (400 MHz, CDCl$_3$): 8.85 (d, 1H), 8.38 (q, 1H), 8.11 (d, 1H), 7.55 (s, 1H), 7.40 (s, 2H), 2.33 (s, 6H) ppm.

Analogous procedures were used to prepare the following compounds:

4-Cyano-N[2,6-diethyl-4-(1,2,2,2-tetrafluoro-1-trifluoromethyl-ethyl)-phenyl]-3-nitro-benzamide. $^1$H-NMR (400 MHz, CDCl$_3$): 8.84 (s, 1H), 8.38 (q, 1H), 8.10 (d, 1H), 7.57 (bs, 1H), 7.43 (s, 2H), 2.68 (q, 4H), 1.24 (t, 6H) ppm.

4-Cyano-N[2-methoxymethyl-6-methyl-4-(1,2,2,2-tetrafluoro-1-trifluoromethyl-ethyl)-phenyl]-3-nitro-benzamide. $^1$H-NMR (400 MHz, CDCl$_3$): 9.18 (s, 1H), 8.88 (s, 1H), 8.39 (d, 1H), 8.11 (d, 1H), 7.55 (s, 2H), 7.40 (s, 1H), 4.55 (s, 2H), 3.45 (s, 3H), 2.39 (s, 3H) ppm.

N[2-Bromo-6-methyl-4-(1,2,2,2-tetrafluoro-1-tri fluoromethyl-ethyl)-phenyl]-4-cyano-3-nitro-benzamide. $^1$H-NMR (400 MHz, CDCl$_3$): 8.88 (s, 1H), 8.40 (d, 1H), 8.11 (d, 1H), 7.78 (s, 2H), 7.52 (s, 1H), 2.44 (s, 3H) ppm.

N-[2-Bromo-6-ethyl-4-(1,2,2,2-tetrafluoro-1-trifluoromethyl-ethyl)-phenyl]-4-cyano-3-nitro-benzamide. $^1$H-1-

NMR (400 MHz, CDCl$_3$): 8.87 (s, 1H), 8.39 (d, 1H), 8.10 (d, 1H), 7.80 (s, 1H), 7.74 (s, 1H), 7.56 (s, 1H), 2.77 (q, 2H), 1.29 (t, 3H) ppm.

4-Cyano-N[2,6-dibromo-4-(1,2,2,2-tetrafluoro-1-trifluoromethyl-ethyl)-phenyl]-3-nitro-benzamide. This was used in the next step without further purification.

4-Cyano-N-[2-ethyl-6-methyl-4-(1,2,2,3,3,3-hexafluoro-1-trifluoromethyl-propyl)-phenyl]-3-nitro-benzamide. $^1$H-NMR (400 MHz, CDCl$_3$): 8.86 (s, 1H), 8.39 (q, 1H), 8.10 (d, 1H), 7.80 (s, 1H), 7.39 (s, 2H), 2.68 (q, 2H), 2.32 (s, 3H), 1.20 (t, 3H) ppm.

4-Cyano-N-[2,6-diethyl-4-(1,2,2,3,3,3-hexafluoro-1-trifluoromethyl-propyl)-phenyl]-3-nitro-benzamide. $^1$H-NMR (400 MHz, CDCl$_3$): 8.84 (s, 1H), 8.38 (q, 1H), 8.11 (d, 1H), 7.63 (s, 1H), 7.26 (s, 2H), 2.67 (q, 4H), 1.23 (t, 6H) ppm.

2-Cyano-N-[2,6-dimethyl-4-(1,2,2,2-tetrafluoro-1-trifluoromethyl-ethyl)-phenyl]-5-nitro-benzamide. $^1$H-NMR (400 MHz, CDCl$_3$): 8.81 (m, 1H), 8.69 (m, 1H), 8.33 (d, 1H), 7.49 (s, 2H), 2.21 (s, 6H) ppm.

2-Cyano-N-[2,6-diethyl-4-(1,2,2,2-tetrafluoro-1-trifluoromethyl-ethyl)-phenyl]-3-nitro-benzamide. $^1$H-NMR (400 MHz, CDCl$_3$): 10.67 (s, 1H), 8.58 (d, 1H), 8.40 (d, 1H), 8.02 (t, 1H), 7.49 (s, 2H), 2.53 (q, 4H), 1.17 (t, 6H) ppm.

Example I2

Preparation of 3-amino-4-cyano-n[2,6-dimethyl-4-(1,2,2,2-tetrafluoro-1-tri-fluoromethyl-ethyl)-phenyl]-benzamide

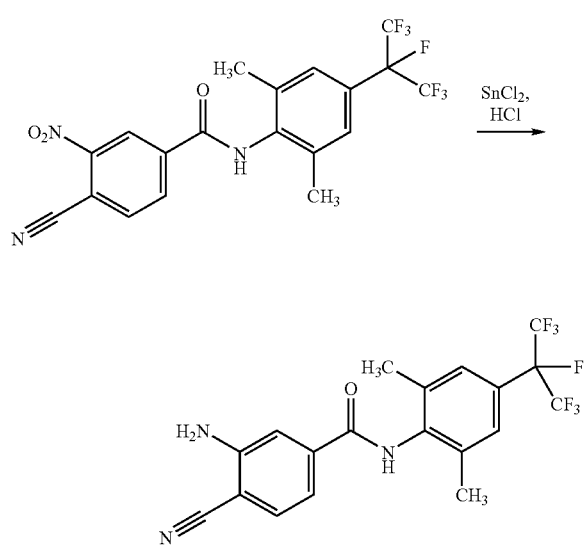

4-Cyano-N-[2,6-dimethyl-4-(1,2,2,2-tetrafluoro-1-trifluoromethyl-ethyl)-phenyl]-3-nitro-benzamide (1.0 g, 2.16 mmol) (Example D.) was dissolved in diethylene glycol dimethyl ether ("diglyme") (25 ml) and tin chloride (1.229 g, 6.48 mmol) was added. The mixture was cooled to 0° C. and aqueous hydrochloric acid (concentrated) (4 ml) was added slowly. The reaction mixture was stirred at 80° C. for 0.5 hours. Aqueous sodium hydroxide (30% by weight) (80 ml) was added to adjust the pH to 7-8. The aqueous phase was extracted three times with ethyl acetate (200 ml). The combined organic extracts were dried over sodium sulfate and concentrated. The residue was purified by column chromatography on silica gel (eluent: cyclohexane/ethyl acetate 1:1 to 0:1) to give 3-amino-4-cyano-N-[2,6-dimethyl-4-(1,2,2,2-tetrafluoro-1-trifluoromethyl-ethyl)-phenyl]-benzamide (0.48 g, 51% yield). $^1$H-NMR (400 MHz, CDCl$_3$): 7.54 (s, 1H), 7.49 (d, 2H), 7.36 (m, 3H), 7.15 (q, 1H), 2.3 (s, 6H) ppm.

Analogous procedures or well known procedures such as hydrogenation in the presence of a palladium catalyst, as described in, for example, Journal of Medicinal Chemistry (2005), 48(24), 7560 or Journal of Medicinal Chemistry (2005), 48(6), 1729, and reduction with sodium hydrogen sulfite in a biphasic system with tetrabutylammonium bromide as phase transfer catalyst, as described in, for example, Journal of Medicinal Chemistry (2006), 49(3), 955-970, were used to prepare the following compounds:

3-Amino-4-cyano-N[2,6-diethyl-4-(1,2,2,2-tetrafluoro-1-trifluoromethyl-ethyl)-phenyl]-benzamide. $^1$H-NMR (400 MHz, CDCl$_3$): 7.53 (d, 1H), 7.40 (s, 2H), 7.33 (m, 2H), 4.65 (bs, 2H), 2.67 (q, 4H), 1.19 (t, 6H) ppm.

3-Amino-4-cyano-N[2-methoxymethyl-6-methyl-4-(1,2,2,2-tetrafluoro-1-trifluoro-methyl-ethyl)-phenyl]-benzamide. $^1$H-NMR (400 MHz, CDCl$_3$): 8.78 (s, 1H), 7.53 (m, 2H), 7.38 (s, 1H), 7.18 (d, 1H), 4.65 (s, 2H), 4.49 (s, 2H), 3.40 (s, 3H), 2.38 (s, 3H) ppm.

3-Amino-N-[2-bromo-6-methyl-4-(1,2,2,2-tetrafluoro-1-trifluoromethyl-ethyl)-phenyl]-4-cyano-benzamide. $^1$H-NMR (400 MHz, CDCl$_3$): 7.72 (s, 1H), 7.60 (s, 1H), 7.54 (d, 1H), 7.50 (s, 1H), 7.35 (s, 1H), 7.21 (d, 1H), 4.65 (s, 2H), 2.40 (s, 3H) ppm.

3-Amino-N-[2-bromo-6-ethyl-4-(1,2,2,2-tetrafluoro-1-trifluoromethyl-ethyl)-phenyl]-4-cyano-benzamide. $^1$H-NMR (400 MHz, acetone d$^6$): 7.70 (s, 1H), 7.54 (s, 1H), 7.46 (d, 1H), 7.39 (s, 1H), 7.18 (d, 1H), 5.70 (s, 2H), 2.70 (q, 2H), 1.10 (t, 3H) ppm.

3-Amino-4-cyano-N-[2,6-dibromo-4-(1,2,2,2-tetrafluoro-1-trifluoromethyl-ethyl)-phenyl]-benzamide. $^1$H-NMR (400 MHz, CDCl$_3$): 8.88 (s, 2H), 7.63 (s, 1H), 7.54 (d, 1H), 7.35 (s, 1H), 7.21 (d, 1H), 4.67 (bs, 2H) ppm.

3-Amino-4-cyano-N-[2-ethyl-6-methyl-4-(1,2,2,3,3,3-hexafluoro-1-trifluoromethyl-propyl)-phenyl]-benzamide. $^1$H-NMR (400 MHz, CDCl$_3$): 7.53 (d, 1H), 7.33 (m, 4H), 7.15 (q, 1H), 4.64 (bs, 2H), 2.67 (q, 2H), 2.33 (s, 3H), 1.21 (t, 3H) ppm.

3-Amino-4-cyano-N-[2,6-diethyl-4-(1,2,2,3,3,3-hexafluoro-1-trifluoromethyl-propyl)-phenyl]-benzamide. $^1$H-NMR (400 MHz, CDCl$_3$): 7.74 (d, 1H), 7.38 (s, 2H), 7.34 (m, 2H), 7.15 (q, 1H), 4.66 (bs, 2H), 2.66 (q, 4H), 1.21 (t, 6H) ppm.

5-Amino-2-cyano-N-[2,6-dimethyl-4-(1,2,2,2-tetrafluoro-1-trifluoromethyl-ethyl)-phenyl]-benzamide. $^1$H-NMR (400 MHz, CDCl$_3$): 7.7 (s, 1H), 7.43 (s, 2H), 7.14 (d, 1H), 7.98 (m, 1H), 4.3 (s, 2H), 2.2 (s, 6H) ppm.

3-Amino-2-cyano-N-[2,6-diethyl-4-(1,2,2,2-tetrafluoro-1-trifluoromethyl-ethyl)-phenyl]-benzamide. $^1$H-NMR (400

MHz, CDCl$_3$): 7.5-7.44 (m, 4H), 7.28 (s, 1H), 6.94 (d, 1H), 5.60 (s, 2H), 2.50 (q, 4H), 1.13 (t, 6H) ppm.

Example P1

Preparation of 3-amino-4-cyano-N-[2,6-dimethyl-4-(1,2,2,2-tetrafluoro-1-trifluoromethyl-ethyl)-phenyl]-benzamide (Compound No. A1 of Table A)

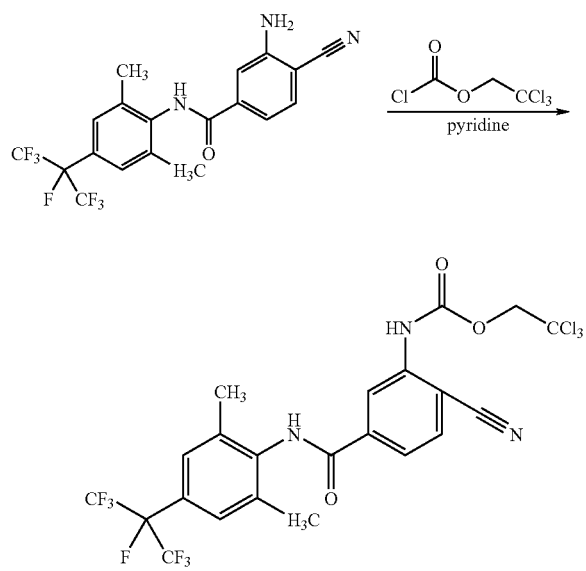

3-Amino-4-cyano-N[2,6-dimethyl-4-(1,2,2,2-tetrafluoro-1-trifluoromethyl-ethyl)-phenyl]-benzamide (Example I2) (199 mg, 0.46 mmol) was dissolved in tetrahydrofuran (5 ml), then pyridine (0.074 ml, 0.92 mmol) was added at ambient temperature. Trichloromethyl chloroformate (0.066 ml, 0.48 mmol) was added under vigorous stirring at ambient temperature. The reaction mixture was stirred for 16 hours at ambient temperature. A mixture of ethyl acetate (50 ml) and aqueous sodium hydrogen carbonate (saturated) was added. The phases were separated and the aqueous phase was extracted twice with ethyl acetate (50 ml). The combined organic extracts were dried over sodium sulfate and concentrated. The residue was purified by column chromatography on silica gel (eluent: cyclohexane/ethyl acetate 2:1) to give Compound No. A1 of Table A (0.125 mg, 45% yield).

Analogous procedures were used to prepare the following compounds:

Compound No. A4, A7, and A9 to A14 of Table A, Compound No. C1 of Table C, and Compound No. D1 of Table D. Compound No. A5 was obtained as a by-product in the synthesis of Compound No. A4, and Compound No. A8 was obtained as a by-product in the synthesis of Compound No. A7.

Example I3

Preparation of 4-cyano-N-[2,6-dimethyl-4-(1,2,2,2-tetrafluoro-1-trifluoromethyl-ethyl)-phenyl]-3-methylamino-benzamide

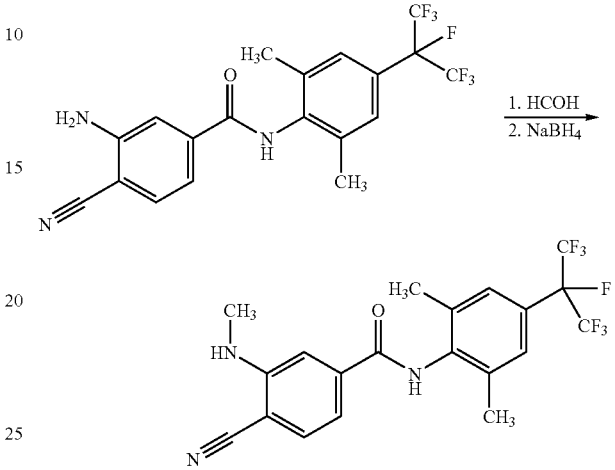

3-Amino-4-cyano-N[2,6-dimethyl-4-(1,2,2,2-tetrafluoro-1-trifluoromethyl-ethyl)-phenyl]-benzamide (3.01 g, 6.95 mmol) (Example I2) was dissolved in acetonitrile (50 ml) and aqueous formaldehyde (36.5% w/v) (0.64 ml, 6.95 mmol) and acetic acid (30 ml) were added successively. The reaction mixture was stirred at ambient temperature for 45 minutes. Then sodium borohydride (0.44 g, 6.95 mmol) and more acetic acid (5 ml) were added. The reaction mixture was stirred at ambient temperature for 2 hours. The reaction mixture was concentrated. The residue was dissolved in ethyl acetate and the solution washed with aqueous sodium hydroxide (1N). The aqueous phase was extracted three times with ethyl acetate (200 ml). The combined organic extracts were dried over sodium sulfate and concentrated. The residue was purified by column chromatography on silica gel (eluent: cyclohexane/ethyl acetate 1:5) to give 4-cyano-N-[2,6-dimethyl-4-(1,2,2,2-tetrafluoro-1-trifluoromethyl-ethyl)-phenyl]-3-methylamino-benzamide (1.80 g, 58% yield). M.p. 204-206° C. $^1$H-NMR (400 MHz, CDCl$_3$): 7.53 (d, 1H), 7.37 (s, 3H), 7.23 (s, 1H), 7.10 (q, 1H), 5.88 (d, 1H), 3.02 (d, 3H), 2.35 (s, 6H) ppm. The method as described in Example P1 was then used to prepare Compound No. A3 of Table A.

An analogous procedure was used to prepare the following compound:

4-Cyano-N[2,6-diethyl-4-(1,2,2,2-tetrafluoro-1-trifluoromethyl-ethyl)-phenyl]-3-methylamino-benzamide. M.p. 199-202° C. $^1$H-NMR (400 MHz, CDCl$_3$): 7.53 (d, 1H), 7.40 (s, 2H), 7.31 (s, 1H), 7.23 (s, 1H), 7.08 (q, 1H), 5.88 (d, 1H), 3.02 (d, 3H), 2.69 (q, 4H), 1.24 (t, 6H) ppm. The method as described in Example P1 was then used to prepare Compound No. A6 of Table A.

An analogous procedure was used to prepare the following compound:

4-Cyano-N-[2,6-dimethyl-4-(1,2,2,2-tetrafluoro-1-trifluoromethyl-ethyl)-phenyl]-3-ethylamino-benzamide using acetaldehyde as reagent. $^1$H-NMR (400 MHz, CDCl$_3$): 7.52 (d, 1H), 7.37 (s, 2H), 7.35 (s, 1H), 7.23 (s, 1H), 7.08 (m, 1H), 4.69 (t, 1H), 3.35 (m, 2l-1), 2.35 (s, 6H), 1.24 (t, 3H) ppm. The method as described in Example P1 was then used to prepare Compound No. A2 of Table A.

Example I4

Preparation of 3-cyano-5-nitro-benzoic acid

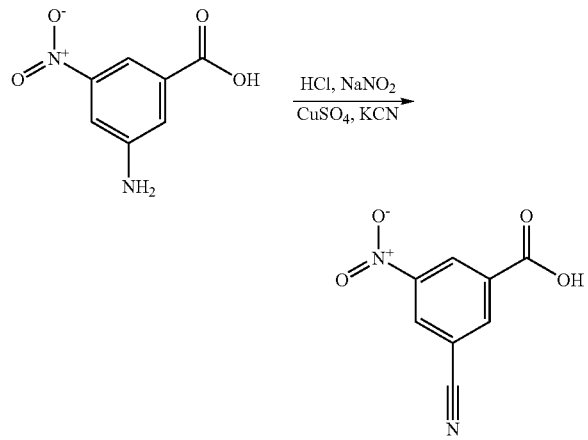

Solution 1: 3-Amino-5-nitro-benzoic acid (10 g, 54.9 mmol) was dissolved in aqueous hydrochloric acid (concentrated) (55 ml) and diluted with water (200 ml). A solution of sodium nitrite (3.788 g, 54.90 mmol) in water (30 ml) was added at 0-5° C.

Solution 2: To a solution of copper sulfate hydrated (28.786 g, 115.29 mmol) in water (120 ml) was added a solution of potassium cyanide (27.528 g, 422.73 mmol) in water (30 ml).

Solution 2 was heated to 65° C. The pH of Solution 1 was adjusted to 6-7 by addition of aqueous sodium carbonate (saturated) at 0-5° C. Solution 1 was added dropwise to Solution 2 at 65° C. The reaction mixture was heated to reflux for 40 minutes. The reaction mixture was allowed to cool to ambient temperature and acidified by addition of aqueous hydrochloric acid (2N). The aqueous phase was extracted with ethyl acetate (3×200 ml) and the combined organic extracts washed with aqueous sodium phosphite (saturated), water, brine and concentrated to give 3-cyano-5-nitro-benzoic acid (7.2 g, 68% yield) which was used without further purification. $^1$H-NMR (400 MHz, DMSO-$d_6$): 9.0 (s, 1H), 8.82 (s, 1H), 8.70 (s, 1H) ppm.

Example I5

Preparation of 3-cyano-N-[2,6-dimethyl-4-(1,2,2,2-tetrafluoro-1-trifluoromethyl-ethyl)-phenyl]-5-nitro-benzamide

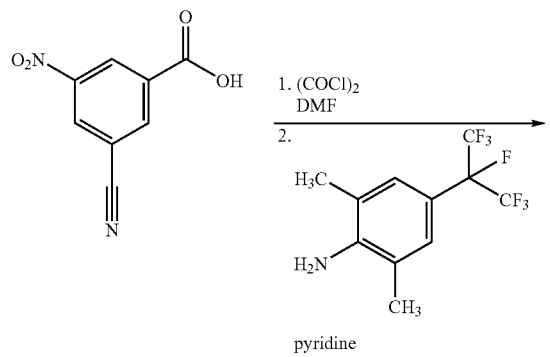

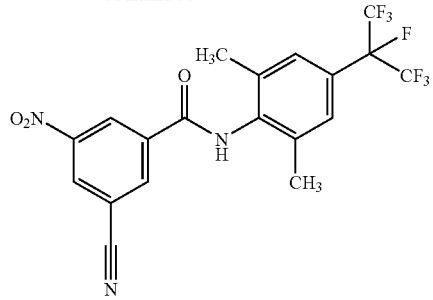

To a suspension of 3-cyano-5-nitro-benzoic acid (Example I4) (7.2 g, 37.5 mmol) in dichloromethane (40 ml) was added oxalyl chloride (3.808 ml, 45 mmol) at ambient temperature, followed by N,N-dimethylformamide ("DMF") (0.2 ml). The reaction mixture was stirred for 1 hour at ambient temperature and then heated to reflux for 3 hours. The reaction mixture was allowed to cool to ambient temperature and then concentrated. The to residue was suspended in tetrahydrofuran (50 ml). 2,6-dimethyl-4-(heptafluoro-prop-2-yl)-aniline (9.761 g, 33.7 mmol) (prepared according to EP 1,006,102) was dissolved in tetrahydrofuran (50 ml) and pyridine (6.035 ml, 75 mmol) was added. The mixture was cooled to 0° C. and the solution of 2-fluoro-5-nitro-benzoyl chloride was added. The reaction mixture was stirred at ambient temperature for 12 hours. Then aqueous sodium hydrogen carbonate (saturated) (100 ml) was added and the organic phase extracted twice with ethyl acetate (2×200 ml). The combined organic extracts were dried over sodium sulfate and concentrated. The residue was purified by column chromatography on silica gel (eluent: cyclohexane/ethyl acetate 6:1) to give 3-cyano-N-[2,6-dimethyl-4-(1,2,2,2-tetrafluoro-1-trifluoromethyl-ethyl)-phenyl]-5-nitro-benzamide (12 g, 77% yield). $^1$H-NMR (400 MHz, CDCl$_3$): 8.99 (m, 1H), 8.72 (m, 1H), 8.6 (m, 1H), 7.80 (s, 1H), 7.4 (s, 2H), 2.33 (s, 6H) ppm.

Example I5

Preparation of 5-amino-3-cyano-N-[2,6-dimethyl-4-(1,2,2,2-tetrafluoro-1-tri-fluoromethyl-ethyl)-phenyl]-benzamide

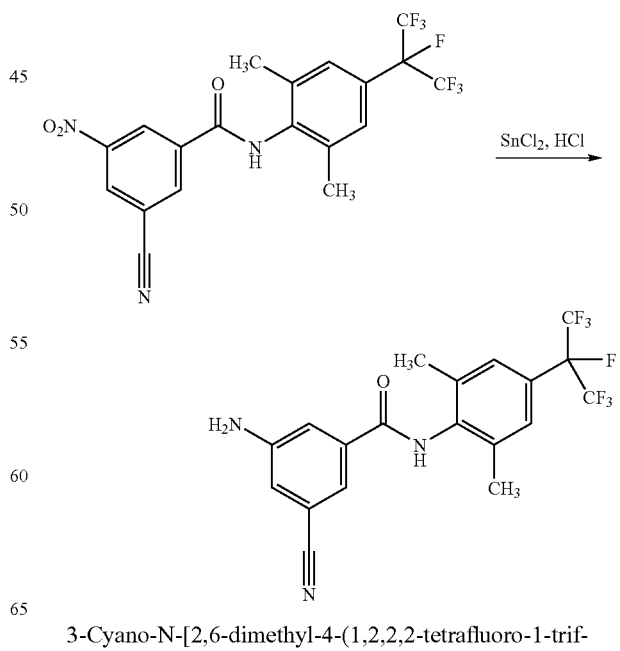

3-Cyano-N-[2,6-dimethyl-4-(1,2,2,2-tetrafluoro-1-trifluoromethyl-ethyl)-phenyl]-5-nitro-benzamide (12.0 g, 25.9 mmol) (Example I5) was dissolved in isopropanol (200 ml) and tin chloride (14.73 g, 77.7 mmol) was added. The mixture was cooled to 0° C. and aqueous hydrochloric acid (concentrated) (30 ml) was added slowly. The reaction mixture was stirred at 80° C. for 0.5 hours. ⅓ of the total volume of isopropanol was evaporated. Water (100 ml) was added to the concentrated mixture and aqueous sodium hydroxide (4N) was added to adjust the pH to 7-8. The aqueous phase was extracted three times with ethyl acetate (3×200 ml). The combined organic extracts were dried over sodium sulfate and concentrated. The residue was purified by column chromatography on silica gel (eluent: cyclohexane/ethyl acetate 4:1 to 0:1) to give 5-amino-3-cyano-N-[2,6-dimethyl-4-(1,2,2,2-tetrafluoro-1-trifluoromethyl-ethyl)-phenyl]-benzamide (10.6 g, 94.4% yield). $^1$H-NMR (400 MHz, CDCl$_3$): 7.47 (s, 1H), 7.44 (s, 2H), 7.36 (s, 2H), 7.07 (s, 1H), 4.11 (bs, 2H), 2.32 (s, 6H) ppm.

Example P2

Preparation of 3-amino-5-cyano-N-[2,6-dimethyl-4-(1,2,2,2-tetrafluoro-1-trifluoromethyl-ethyl)-phenyl]-benzamide (Compound No. B1 of Table B)

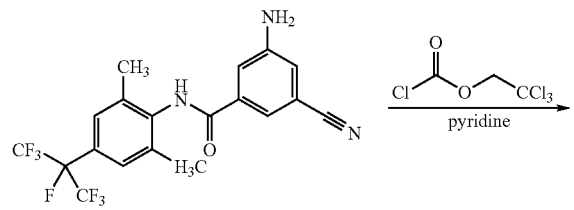

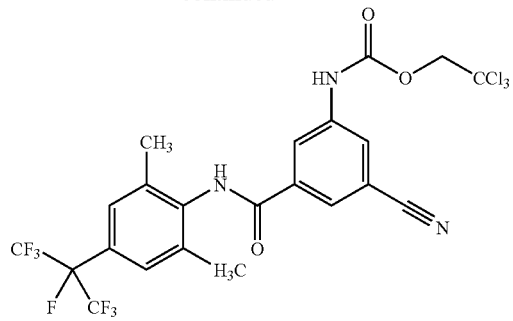

3-Amino-5-cyano-N-[2,6-dimethyl-4-(1,2,2,2-tetrafluoro-1-trifluoromethyl-ethyl)-phenyl]benzamide (Example I5) (199 mg, 0.46 mmol) was dissolved in tetrahydrofuran (3 ml), then pyridine (0.117 ml, 1.45 mmol) was added at ambient temperature. Trichloromethyl chloroformate (0.070 ml, 0.48 mmol) was added under vigorous stirring at ambient temperature. The mixture was stirred for 2 hours at ambient temperature. A mixture of ethyl acetate (50 ml) and aqueous sodium hydrogen carbonate (saturated) was added. The phases were separated and the aqueous phase was extracted twice with ethyl acetate (50 ml). The combined organic extracts were dried over sodium sulfate and concentrated. The residue was purified by chromatography on silica gel (eluent: cyclohexane/ethyl acetate 2:1) to give Compound No. B1 of Table B (210 mg, 74% yield).

TABLE A

Compounds of formula (Ia):

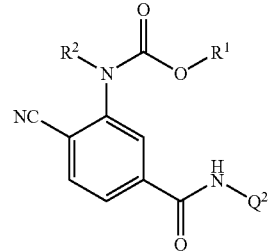

(Ia)

| Comp No. | R$^1$ | R$^2$ | Q$^2$ | M.p. in ° C. | RT/MH+ | $^1$H-NMR (CHCl$_3$, 400 MHz) in ppm |
|---|---|---|---|---|---|---|
| A1 | —CH$_2$—CCl$_3$ | H | 2,6-dimethyl-4-(heptafluoro-prop-2-yl)-phenyl- | — | — | 8.79 (s, 1H), 7.78 (m, 2H), 7.53 (s, 2H), 7.37 (s, 2H), 4.89 (s, 2H), 2.36 (s, 6H). |
| A2 | —CH$_2$—CCl$_3$ | —CH$_2$CH$_3$ | 2,6-dimethyl-4-(heptafluoro-prop-2-yl)-phenyl- | 105 | — | — |
| A3 | —CH$_2$—CCl$_3$ | —CH$_3$ | 2,6-dimethyl-4-(heptafluoro-prop-2-yl)-phenyl- | — | — | 2.33 (6H, s), 3.5 (3H, s), 4.48 (2H, s), 7.39 (3H, m), 7.85-7.98 (3H, m). |
| A4 | —CH$_2$—CCl$_3$ | H | 2,6-diethyl-4-(heptafluoro-prop-2-yl)-phenyl- | 214 | — | — |
| A5 | —CH$_2$—CCl$_3$ | —C(O)—CH$_2$—CCl$_3$ | 2,6-diethyl-4-(heptafluoro-prop-2-yl)-phenyl- | 195 | — | — |

TABLE A-continued

Compounds of formula (Ia):

(Ia)

| Comp No. | R¹ | R² | Q² | M.p. in ° C. | RT/MH+ | ¹H-NMR (CHCl₃, 400 MHz) in ppm |
|---|---|---|---|---|---|---|
| A6 | —CH₂—CCl₃ | —CH₃ | 2,6-diethyl-4-(heptafluoro-prop-2-yl)-phenyl- | — | — | 1.22 (6H, t), 2.67 (4H, q), 3.48 (3H, s), 4.81 (2H, m), 7.40 (3H, m), 7.87-7.98 (3H, m). |
| A7 | —CH₂—CCl₃ | H | 2-methoxy-methyl-6-methyl-4-(heptafluoro-prop-2-yl)-phenyl- | 85 | — | — |
| A8 | —CH₂—CCl₃ | —C(O)—CH₂—CCl₃ | 2-methoxy-methyl-6-methyl-4-(heptafluoro-prop-2-yl)-phenyl- | 86 | — | — |
| A9 | —CH₂—CCl₃ | H | 2-bromo-6-methyl-4-(heptafluoro-prop-2-yl)-phenyl- | — | 2.31/671.9 | — |
| A10 | —CH₂—CCl₃ | H | 2-bromo-6-ethyl-4-(heptafluoro-prop-2-yl)-phenyl- | — | 2.4/685.9 | — |
| A11 | —CH₂—CCl₃ | H | 2,6-dibromo-4-(hepta-fluoro-prop-2-yl)-phenyl- | 208-210 | — | — |
| A12 | —CH₂—CCl₃ | H | 2,6-diethyl-4-(nonafluoro-but-2-yl)-phenyl- | 201 | — | — |
| A13 | —CH₃ | H | 2-ethyl-6-methyl-4-(nonafluoro-but-2-yl)-phenyl- | 182 | — | — |
| A14 | —CH₂—CCl₃ | H | 2-ethyl-6-methyl-4-(nonafluoro-but-2-yl)-phenyl | 194 | — | — |

Key:
s = singlet;
m = multiplet.

TABLE B

Compounds of formula (Ib):

(Ib)

Structure: R²-N(-C(=O)-O-R¹) attached to benzene ring with NC substituent and C(=O)-N(H)-Q² substituent

| Comp No. | R¹ | R² | Q² | ¹H-NMR (CHCl₃, 400 MHz) in ppm |
|---|---|---|---|---|
| B1 | —CH₂CCl₃ | H | 2,6-dimethyl-4-(heptafluoro-prop-2-yl)-phenyl- | 8.19 (s, 1H), 8.07 (s, 1H), 7.93 (s, 1H), 7.56 (s, 1H), 7.37 (m, 3H), 4.86 (s, 2H), 2.34 (s, 6H). |

Key:
s = singlet;
m = multiplet.

TABLE C

Compounds of formula (Ic):

(Ic)

| Comp No. | R¹ | R² | Q² | M.p. in ° C. |
|---|---|---|---|---|
| C1 | —CH₂CCl₃ | H | 2,6-dimethyl-4-(heptafluoro-prop-2-yl)-phenyl- | 208 |

TABLE D

Compounds of formula (Id):

(Id)

| Comp No. | R¹ | R² | Q² | M.p. in ° C. |
|---|---|---|---|---|
| D1 | —CH₂CCl₃ | H | 2,6-diethyl-4-(heptafluoro-prop-2-yl)-phenyl- | 139 |

Biological Examples

This Example illustrates the pesticidal/insecticidal properties of compounds of formula (I). Test against were performed as follows:

*Spodoptera Littoralis* (Egyptian Cotton Leafworm)

Cotton leaf discs were placed on agar in a 24-well microtiter plate and sprayed with test solutions at an application rate of 200 ppm. After drying, the leaf discs were infested with 5 L1 larvae. The samples were checked for mortality, feeding behaviour, and growth regulation 3 days after treatment (DAT).

The following compounds gave at least 80% control of *Spodoptera littoralis*: A1, A2, A3, A4, A5, A6, A7, A8, A11, A12, A13, A14, B1, D1.

*Heliothis Virescens* (Tobacco Budworm):

Eggs (0-24 h old) were placed in 24-well microtiter plate on artificial diet and treated with test solutions at an application rate of 200 ppm (concentration in well 18 ppm) by pipetting. After an incubation period of 4 days, samples were checked for egg mortality, larval mortality and growth regulation.

The following compounds gave at least 80% control of *Heliothis virescens*: A1, A2, A3, A4, A5, A6, A7, A8, A11, A12, A13, A14, B1.

*Plutella Xylostella* (Diamond Back Moth):

A 24-well microtiter plate (MTP) with artificial diet was treated with test solutions at an application rate of 200 ppm (concentration in well 18 ppm) by pipetting. After drying, the MTP's were infested with L2 larvae (7-12 per well). After an incubation period of 6 days, samples were checked for larval mortality and growth regulation.

The following compounds gave at least 80% control of *Plutella xylostella*: A1, A2, A3, A4, A6, A7, A8, A11, A12, A13, A14, B1.

*Diabrotica Balteata* (Corn Root Worm):

A 24-well microtiter plate (MTP) with artificial diet was treated with test solutions at an application rate of 200 ppm (concentration in well 18 ppm) by pipetting. After drying, the MTP's were infested with larvae (L2) (6-10 per well). After an incubation period of 5 days, samples were checked for larval mortality, and growth regulation.

The following compounds gave at least 80% control of *Diabrotica balteata*: A1, A2, A3, A4, A5, A6, A7, A8, A11, A12, A13, A14, B1.

*Myzus Persicae* (Green Peach Aphid):

Sunflower leaf discs were placed on agar in a 24-well microtiter plate and sprayed with test solutions at an application rate of 200 ppm. After drying, the leaf discs were infested with an aphid population of mixed ages. After an incubation period of 6 DAT, samples were checked for mortality.

The following compounds gave at least 80% control of *Myzus persicae*: A12.

*Thrips Tabaci* (Onion Thrips):

Sunflower leaf discs were placed on agar in a 24-well microtiter plate and sprayed with test solutions at an application rate of 200 ppm. After drying, the leaf discs were infested with an aphid population of mixed ages. After an incubation period of 7 days, samples were checked for mortality.

The following compounds gave at least 80% control of *Thrips tabaci*: A8, A11, A12, A14.

*Tetranychus Urticae* (Two-Spotted Spider Mite):

Bean leaf discs on agar in 24-well microtiter plates were sprayed with test solutions at an application rate of 200 ppm. After drying, the leaf discs are infested with mite populations of mixed ages. 8 days later, discs are checked for egg mortality, larval mortality, and adult mortality.

The following compounds gave at least 80% control of *Tetranychus urticae*: A11.

The invention claimed is:
1. A compound of formula (I):

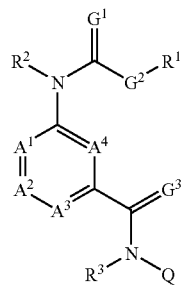

wherein
$A^1, A^2, A^3$ and $A^4$ are independently of each other C—$R^4$, C—$R^5$ or nitrogen, provided that at least one of $A^1, A^2, A^3$ and $A^4$ is C—$R^4$ and no more than two of $A^1, A^2, A^3$ and $A^4$ are nitrogen;
$R^1$ is $C_1$-$C_6$alkyl, $C_1$-$C_6$haloalkyl, $C_2$-$C_6$alkenyl, $C_2$-$C_6$haloalkenyl, $C_2$-$C_6$alkynyl, $C_2$-$C_6$haloalkynyl, $C_3$-$C_8$cycloalkyl, $C_3$-$C_8$halocycloalkyl, or -$E^1$-$Z^1$—$R^6$ wherein $E^1$ its $C_1$-$C_4$alkylene, $C_2$-$C_4$alkenylene, $C_3$-$C_4$alkynylene, $C_1$-$C_4$haloalkylene, $C_2$-$C_4$haloalkenylene, or $C_3$-$C_4$haloalkynylene, $Z^1$ is —O—, —S—, —SO—, or —$SO_2$—, and $R^6$ is hydrogen, $C_1$-$C_6$alkyl, $C_2$-$C_6$alkenyl, $C_2$-$C_6$alkynyl, $C_1$-$C_6$haloalkyl, $C_2$-$C_6$haloalkenyl, $C_2$-$C_6$haloalkynyl, or -$E^2$-$R^7$ wherein $E^2$ is $C_1$-$C_4$alkylene, $C_2$-$C_4$alkenylene, $C_3$-$C_4$alkynylene, $C_1$-$C_4$haloalkylene, $C_2$-$C_4$haloalkenylene, or $C_3$-$C_4$haloalkynylene, and $R^7$ is $C_3$-$C_8$cycloalkyl, $C_3$-$C_8$halocycloalkyl, cyano, nitro, hydroxyl, or phenyl or phenyl substituted by one to five substituents $R^8$, which may be the same or different, or pyridyl or pyridyl substituted with one to four substituents $R^9$, which may be the same or different, or thiophenyl, or tetrahydrofuranyl;
$R^2$ and $R^3$ are independently of each other hydrogen, $C_1$-$C_4$alkyl, $C_2$-$C_4$alkenyl, $C_2$-$C_4$alkynyl, $C_1$-$C_4$alkylcarbonyl, $C_1$-$C_4$haloalkylcarbonyl, hydroxy, $C_1$-$C_4$alkylcarbonyloxy, arylcarbonyloxy or arylcarbonyloxy wherein the aryl ring is substituted by one to five substituents independently selected from halogen, $C_1$-$C_4$alkyl, $C_1$-$C_4$haloalkyl, $C_1$-$C_4$alkoxy or $C_1$-$C_4$haloalkoxy;
$G^1, G^2$ and $G^3$ are independently of each other oxygen or sulfur;
each $R^4$ is independently cyano, thiocyanato, aminothiocarbonyl, N—$C_1$-$C_4$alkyl-aminothiocarbonyl or N,N-di-$C_1$-$C_4$alkyl-aminothiocarbonyl;
each $R^5$ is independently hydrogen, halogen, $C_1$-$C_4$alkyl, $C_1$-$C_4$haloalkyl or $C_1$-$C_4$alkoxy;
each $R^8$ is independently halogen, $C_1$-$C_6$alkyl, $C_1$-$C_6$haloalkyl, $C_1$-$C_6$alkoxy, $C_1$-$C_6$haloalkoxy, $C_1$-$C_6$alkylthio, $C_1$-$C_6$halo alkylthio, $C_1$-$C_6$alkylsulfinyl, $C_1$-$C_6$haloalkylsulfinyl, $C_1$-$C_6$alkylsulfonyl, $C_1$-$C_6$haloalkylsulfonyl, cyano, nitro, hydroxyl, $C_1$-$C_4$alkylcarbonyl, $C_1$-$C_4$haloalkylcarbonyl, $C_1$-$C_4$alkylcarbonyloxy, $C_1$-$C_4$alkoxycarbonyl, or pentafluorosulfanyl;

each $R^9$ is independently halogen, $C_1$-$C_6$alkyl, $C_1$-$C_6$haloalkyl, $C_1$-$C_6$alkoxy, $C_1$-$C_6$haloalkoxy, $C_1$-$C_6$alkylthio, $C_1$-$C_6$haloalkylthio, $C_1$-$C_6$alkylsulfinyl, $C_1$-$C_6$haloalkylsulfinyl, $C_1$-$C_6$alkylsulfonyl, $C_1$-$C_6$haloalkylsulfonyl, cyano, nitro, hydroxyl, $C_1$-$C_4$alkylcarbonyl, $C_1$-$C_4$haloalkylcarbonyl, $C_1$-$C_4$alkylcarbonyloxy, $C_1$-$C_4$alkoxycarbonyl, or pentafluorosulfanyl; and
Q is a moiety of formula (II) or (III)

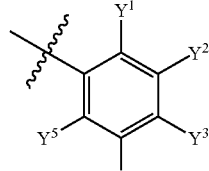

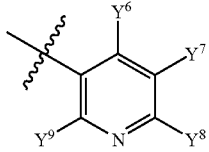

wherein
$Y^1, Y^2, Y^4$ and $Y^5$ are independently of each other hydrogen, halogen, $C_1$-$C_6$alkyl, $C_1$-$C_6$-haloalkyl, $C_1$-$C_4$alkoxy-$C_1$-$C_4$-alkyl, $C_1$-$C_6$alkoxy, $C_1$-$C_6$haloalkoxy, $C_1$-$C_6$alkylthio, $C_1$-$C_6$haloalkylthio, $C_1$-$C_6$alkylsulfinyl, $C_1$-$C_6$halo alkylsulfinyl, $C_1$-$C_6$alkylsulfonyl, $C_1$-$C_6$haloalkylsulfonyl, pentafluorosulfanyl, cyano, or nitro, provided that no more than one of $Y^1$ and $Y^5$ is hydrogen,
$Y^3$ is $C_1$-$C_6$haloalkyl, $C_1$-$C_6$haloalkoxy, $C_1$-$C_6$hydroxyhaloalkyl, $C_1$-$C_6$haloalkylthio, $C_1$-$C_6$haloalkylsulfinyl, $C_1$-$C_6$haloalkylsulfonyl, or pentafluorosulfanyl,
$Y^6, Y^7$ and $Y^9$ are independently of each other hydrogen, $C_1$-$C_6$alkyl, $C_1$-$C_6$haloalkyl, $C_1$-$C_{14}$alkoxy-$C_1$-$C_4$-alkyl, $C_1$-$C_6$alkoxy, $C_1$-$C_6$halo alkoxy, $C_1$-$C_{16}$alkylthio, $C_1$-$C_6$halo alkylthio, $C_1$-$C_6$alkylsulfinyl, $C_1$-$C_6$halo alkylsulfinyl, $C_1$-$C_6$alkylsulfonyl, $C_1$-$C_6$halo alkylsulfonyl, pentafluorosulfanyl, cyano, or nitro, provided that no more than one of $Y^6$ and $Y^9$ is hydrogen, and
$Y^8$ is $C_1$-$C_6$haloalkyl, $C_1$-$C_6$haloalkoxy, $C_1$-$C_6$hydroxyhaloalkyl, $C_1$-$C_6$haloalkylthio, $C_1$-$C_6$haloalkylsulfinyl, $C_1$-$C_6$haloalkylsulfonyl, or pentafluorosulfanyl;
or a salt or N-oxide of said compound.

2. A compound according to claim 1 wherein $A^1$ is C—$R^4$ or C—$R^5$.

3. A compound according to claim 1 wherein $A^2$ is C—$R^4$ or C—$R^5$.

4. A compound according to claim 1 wherein $A^3$ is C—$R^4$ or C—$R^5$.

5. A compound according to claim 1 wherein $A^4$ is C—$R^4$ or C—$R^5$.

6. A compound according to claim 1 wherein one, two or three of $A^1, A^2, A^3$ and $A^4$ are C—$R^4$.

7. A compound according to claim 1 wherein $R^1$ is $C_1$-$C_6$alkyl, $C_1$-$C_6$haloalkyl, $C_2$-$C_6$alkenyl, $C_2$-$C_6$haloalkenyl, $C_2$-$C_6$alkynyl, $C_2$-$C_6$haloalkynyl, $C_3$-$C_8$cycloalkyl, $C_3$-$C_8$halocycloalkyl, or cyano-$C_1$-$C_4$alkylene.

8. A compound according to claim 1 wherein $R^2$ is hydrogen, methyl, ethyl, allyl, propargyl, acetyl, 3,3,3-trichloropropionyl, hydroxy, acetyloxy or benzoyloxy.

9. A compound according to claim 1 wherein $R^3$ is hydrogen, methyl, ethyl, allyl, propargyl, acetyl, hydroxy, acetyloxy or benzoyloxy.

10. A compound according to claim 1 wherein $G^1$ is oxygen.

11. A compound according to claim 1 wherein $G^2$ is oxygen.

12. A compound according to claim 1 wherein $G^3$ is oxygen.

13. A compound according to claim 1 wherein $R^4$ is independently cyano, thiocyanato or aminothiocarbonyl.

14. A compound according to claim 1 wherein each $R^5$ is independently hydrogen, fluoro, chloro, bromo, methyl, trifluoromethyl or methoxy.

15. A compound according to claim 1 wherein Q is a moiety of formula (II).

16. A method of combating and controlling insects, acarines, nematodes or molluscs which comprises applying to a pest, to a locus of a pest, or to a plant susceptible to attack by a pest an insecticidally, acaricidally, nematicidally or molluscicidally effective amount of a compound of formula (I) as defined in claim 1.

17. An insecticidal, acaricidal or nematicidal composition comprising an insecticidally, acaricidally or nematicidally effective amount of a compound of formula (I) as defined in claim 1.

18. A compound according to claim 1 wherein $A^1$ is C—$R^4$; $A^2$, $A^3$ and $A^4$ are each independently C—$R^5$; $G^1$, $G^2$ and $G^3$ are each oxygen; $R^1$ is $C_1$-$C_6$alkyl or $C_1$-$C_6$haloalkyl; $R^2$ and $R^3$ are each hydrogen; $R^4$ is independently cyano, thiocyanato or aminothiocarbonyl; each $R^5$ is hydrogen; Q is a moiety of formula (II); $Y^1$, $Y^2$, $Y^4$ and $Y^5$ are independently of each other hydrogen and $C_1$-$C_6$alkyl; and $Y^3$ is $C_1$-$C_6$haloalkyl.

19. A compound according to claim 18 wherein $R^1$ is $C_1$-$C_6$haloalkyl; and $Y^1$, $Y^2$, $Y^4$ and $Y^5$ are independently of each other hydrogen and methyl.

20. A compound according to claim 19 wherein $R^1$ is —$CH_2CCl_3$; $R^4$ is cyano; $Y^1$ and $Y^5$ are each methyl, and $Y^2$ and $Y^4$ are each hydrogen; and $Y^3$ is —$CF(CF_3)CF_3$.

* * * * *